United States Patent [19]
Sammes et al.

[11] Patent Number: 5,827,653
[45] Date of Patent: Oct. 27, 1998

[54] NUCLEIC ACID DETECTION WITH ENERGY TRANSFER

[75] Inventors: Peter George Sammes, Farnham Royal; Andrew John Garman, Chester, both of United Kingdom

[73] Assignee: Zeneca Limited, London, England

[21] Appl. No.: 619,724

[22] PCT Filed: Sep. 23, 1994

[86] PCT No.: PCT/GB94/02068

§ 371 Date: May 20, 1996

§ 102(e) Date: May 20, 1996

[87] PCT Pub. No.: WO95/08642

PCT Pub. Date: Mar. 30, 1995

[30] Foreign Application Priority Data

Sep. 23, 1993 [GB] United Kingdom .................. 9319826
Jun. 16, 1994 [GB] United Kingdom .................. 9412106

[51] Int. Cl.⁶ .............................. C12Q 1/68; C09K 3/00; C07H 21/04; C12N 15/00
[52] U.S. Cl. ........................ 435/6; 435/91.1; 435/91.2; 435/810; 436/164; 436/805; 252/700; 536/24.3; 536/26.6; 935/8; 935/77; 935/78
[58] Field of Search ............................. 435/6, 91.1, 91.2, 435/810, 183; 436/164, 73, 94, 172, 800, 805; 252/700; 536/24.3, 26.6; 935/8, 76, 77, 78

[56] References Cited

U.S. PATENT DOCUMENTS

| 4,665,184 | 5/1987 | Dervan et al. ........................ 546/109 |
|---|---|---|
| 4,942,227 | 7/1990 | Dervan et al. ............................ 536/27 |
| 4,954,714 | 9/1990 | Pollak et al. .......................... 250/458.1 |
| 5,565,554 | 10/1996 | Glazer et al. .......................... 536/26.6 |
| 5,571,897 | 11/1996 | Takalo et al. ............................. 534/15 |
| 5,578,498 | 11/1996 | Singh et al. ............................. 436/518 |

FOREIGN PATENT DOCUMENTS

| 144 914 | 6/1985 | European Pat. Off. . |
|---|---|---|
| 171 978 | 2/1986 | European Pat. Off. . |
| 242 527 | 10/1987 | European Pat. Off. . |
| 41 19 075 | 12/1992 | Germany . |
| 89 04375 | 5/1989 | WIPO . |
| 89/04375 | 5/1989 | WIPO . |
| WO 92/16840 | 10/1992 | WIPO . |

OTHER PUBLICATIONS

J. Coates et al, "A New Homogeneous Identification Method For DNA", J. Chem. Soc., Chem. Commun., 1994, pp. 2311–2312.

Angewandte Chemie.International Edition, vol. 29, No. 10, 1990, Weinheim De, pp. 1167–1169, Oser and Valet "Non-radioactive assay of DNA hybridisation by DNA–(template–mediated formation of a ternary Tb III complex in pure liquied phase".

*Primary Examiner*—Bradley L. Sisson
*Attorney, Agent, or Firm*—Cushman Darby & Cushman Intellectual Property Group of Pillsbury Madison & Sutro, LLP

[57] ABSTRACT

A method for the detection of a nucleic acid analyte by complementary probe hybridisation and formation of a chelated lanthanide complex which, upon irradiation by light, results in a characteristic delayed luminescence emission.

33 Claims, 3 Drawing Sheets

SEQUENCE LISTING
( 1 ) GENERAL INFORMATION:
( i i i ) NUMBER OF SEQUENCES: 9
( 2 ) INFORMATION FOR SEQ ID NO:1:
( i ) SEQUENCE CHARACTERISTICS:
( A ) LENGTH: 24 base pairs
( B ) TYPE: nucleic acid
( C ) STRANDEDNESS: single
( D ) TOPOLOGY: linear (x i) SEQUENCE DESCRIPTION: SEQ ID NO:1:

GAGATCAACG AGCAAGAATT TCTT 24

(2) INFORMATION FOR SEQ ID NO:2:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (x i) SEQUENCE DESCRIPTION: SEQ ID NO:2:

GCTAAAGAAA TTCTTGCTCG TTGATCTCCA CT 32

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (x i) SEQUENCE DESCRIPTION: SEQ ID NO:3:

GATCATTCAT GACATTTTAA AAATTACAGG 30

(2) INFORMATION FOR SEQ ID NO:4:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (x i) SEQUENCE DESCRIPTION: SEQ ID NO:4:

GCTAAAGAAA TTCTTGCTCG TTGACCTCCA CT 32

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (x i) SEQUENCE DESCRIPTION: SEQ ID NO:5:

GAGGTCAACG AGCAAGAATT TCTTGC 26

(2) INFORMATION FOR SEQ ID NO:6:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (x i) SEQUENCE DESCRIPTION: SEQ ID NO:6:

GCTAAAGAAA TTCTTGCTCG TTGACCTCCA CT 32

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (x i) SEQUENCE DESCRIPTION: SEQ ID NO:7:

GTGGTAATTT CTTTTATAGT AGAA                                    24

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:8:

CACCATTAAA GAAAATATCA TCTT                                     24

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:9:

GGGGAATCAC CTTCTGTCTA CAAT                                     24

NUCLEIC ACID DETECTION WITH ENERGY TRANSFER

A method is disclosed for the detection of analytes such as DNA or RNA sequences. The method involves forming a complex comprising the analyte and a complementary binding entity such that, for DNA or RNA, hybridisation occurs to form a duplex. Observation of the matching complex is obtained by adding a third, sensitising component that either intercalates or groove binds with the duplex sequence (the duplex binder). The complementary binding entity is designed to incorporate a lanthanide ion and the duplex binder incorporates a ligand for the lanthanide ion that can also act as a sensitiser. Alternatively the complementary binding entity can be attached to the sensitiser and the duplex binder to the lanthanide ligand. When binding in the collaborative manner is achieved, the three component system is irradiated with light which can be selectively absorbed by the sensitiser. The excited sensitiser can donate its energy to the lanthanide ion by a direct ligand to metal energy transfer mechanism such that the lanthanide ion becomes excited. Subsequent emission of light from the excited lanthanide ion signals the formation of the complex and hence the presence of the analyte. Luminescence from the lanthanide species is characterised by a long lifetime, involving a delayed emission process, which can be measured after decay of background fluorescence signals. The method may be applied to either heterogeneous or, preferably, homogeneous assays and may be used either qualitatively or quantitatively.

Methods for the in vitro detection of analytes are well known in the art. The methods include the formation of antibody-antigen complexes, as in immunoassays, and the formation of nucleic acid complexes, as in polynucleotide hybridisation. Polynucleotide hybridisation assays using a polynucleotide probe for verifying the presence of a target polynucleotide target is a well known method. Polynucleotide hybridisation is based upon the ability of a DNA or RNA sequence to form complexes with a complementary dna or rna strand. When single stranded polynucleotide probes are incubated in solution with single stranded target molecules under defined conditions, complementary base sequences-pair to form double-stranded hybrid molecules. Such hybridisation can occur in solution. Alternatively, either the target strand or the probe may be immobilised on a support in which case hybridisation leads to double stranded hybrid molecules which are thus immobilised. In this case any unbound polynucleotide molecules may be washed off whilst leaving the separated, immobilised duplex polynucleotide bound to the support. [See M. Grunstein and J. Wallis, Methods in Enzymology, 1979, 68, pp. 379–469; A. R. Sambrook, Methods in Enzymology, 1980, 65 (part 1), pp. 468–478; 'Modified Nucleotides and Methods of Preparing and Using the Same', by D. C. Ward, A. A. Waldrop and P. R. Langer, European Patent Publication, 063,879; 'DNA Probes for Infectious Disease' by A. J. Berry, and J. B. Peter, Diagnostic Medicine, 1984, March, pp. 1–8.]

The polynucleotide probes comprise a polynucleotide segment and a latent signalling segment which is attached to the polynucleotide. The polynucleotide segment of the probe has the ability to hybridise (base pair) to a complementary sequence of interest within the target polynucleotide (the target). The latent signalling portion of the probe produces the means by which the presence of the analyte can be verified. Whilst methods can involve, for example, fluorescence, phosphorescence, radioactivity, chromogen formation or electron density, this application concerns the use of delayed luminescence.

The method for detecting the presence of a target polynucleotide generally involves several steps, one of which involves the separation of hybridised polynucleotide probe from the unhybridised probe or mismatched target, as in heterogeneous or sandwich type assays. Typically, double stranded polynucleotides are isolated from a sample suspected of containing a target polynucleotide sequence. The double stranded polynucleotides are cut into smaller segments by means of restriction endonuclease enzyme digestion, the segments are separated by gel electrophoresis and the segments transferred from the gel, if needs be onto a support, for example, nitrocellulose paper.

Alternatively, the double stranded polynucleotides are either fixed directly onto the support without any prior enzyme digestion or taken into a solution. If necessary the concentration of the target polynucleotide can be increased by use of standard amplification methods such as the use of the polymerase chain reaction methodology (PCR) [European Patent Application 0201184; see 'PCR Technology' ed. H. A. Erlich, Stockton Press, New York, 1989] before conducting the hybridisation with the probe polynucleotide in the manner described above. The fixed, or free polynucleotides are contacted with a solution containing the polynucleotide probe and the support or solution is heated to 50°–95° C. to denature the polynucleotide double strands. The system is then allowed to cool to an appropriate temperature for an appropriate time to allow hybridisation to take place. An advantage of the heterogeneous method using either bound target or probe polynucleotide is that, after hybridisation, the fixed hybridised polynucleotides can be washed to remove all unbound polynucleotides. However, a disadvantage of the heterogeneous method is that it is time consuming and one cannot be certain that all unbound material is completely removed during the washings. For this reason means for accomplishing direct, homogeneous detection of the complementary hybrid target to probe sequence are desirable. For homogeneous assays only a single addition of reagents to the target polynucleotide is generally required with the consequent saving of time and labour and pretreatments, such as separation, washing and electrophoretic steps, are not required before measurement of the luminescence. Furthermore, such homogeneous assays lend themselves more easily to automated methods for the processing of large numbers of samples.

Several methods seeking to overcome the limitations of heterogeneous assays by use of a homogeneous process have been reported (see for example Matthews J. A. et al, Anal.Biochem., 1988, 169, 1–25). One method comprises the hybridisation of two single stranded probe polynucleotides, both of which contain light-sensitive labels, with a complementary single-stranded polynucleotide target from a sample such that non-radiative energy transfer occurs between the light-sensitive labels of the first and second polynucleotide probes. At least one of the light sensitive labels is of the absorber-emitter type such that energy absorbed by this label from the emission of the other light-sensitive label is reemitted at a different wavelength. These secondary emissions can only occur if hybridisation of both the first and the second single-stranded polynucleotide probes to the target polynucleotide has taken place. The quantity of the target polynucleotides in the sample is related to the amount of secondary light emitted. [See European Patent Publication No. 070,685.] A drawback of this method is that it requires two separate polynucleotide strands to detect the presence of a target polynucleotide. Furthermore the method requires the presence of either light sensitive probes that have completely different light absorbance properties, so that no direct excitation of the second label occurs and only energy transfer from the first to the second label is possible, or the presence of chemiluminescent reagents as well as an absorber-emitter, emission being promoted by the addition of a chemiluminescent catalyst. For the latter method only one label can be attached per polynucleotide probe because the light-sensitive label is attached to the sugar moiety of a terminal nucleoside.

Another method for the detection of a target polynucleotide by means of a homogeneous assay involves forming a hybrid between the target polynucleotide and the polynucleotide probe, wherein the hybrid has binding sites for two specific binding reagents, one of which comprises a first label and the other a second label. The interaction of the first and second labels provides a detectable response which is measurably different when the two labelled reagents are both bound to the same hybrid, as compared to when the two labelled reagents are not so bound to the same hybrid. The formation of the hybrid assay product brings the two labels within approximate interaction distance of one another, e.g. as in the cases of sequential catalyst (enzyme) interaction and energy transfer. Since the labels provide a response, which is distinguishable only when the labels are associated with a hybridised probe, no separation step is required. [See European Patent Application No. 144,914.]. This method has two main embodiments. The first embodiment involves the generation of a component which subsequently produces a colour. This embodiment has a drawback in that it requires the use of two distinct chemical reactions, namely, the reaction of the first label to produce a diffusible mediator product and the reaction of the mediator product with the second label to yield a detectable product. In addition, detection depends on the formation and maintenance of a higher localised concentration of the mediator product in the vicinity of the label as compared to elsewhere in the solution. Furthermore, both reactions require the use of bulky enzyme molecules attached to the polynucleotide probe. These bulky molecules may sterically clash with each other.

A second embodiment involves that of energy transfer, namely the emission of photons from a first label, for example, fluorescence, followed by absorption of the photons by a second label, to either quench the emission or to provide a second emission. This has a drawback in that the efficiencies of such energy transfer processes are generally low, leading to low sensitivities of the method. Furthermore, background fluorescence together with adventitious excitation of the second label by background fluorescence also detracts from the specificity of the method.

European Patent application no. 242,527 details a through space energy transfer process; this contains as an embodiment, the use of lanthanide species as the energy acceptor by a through space energy coupling mechanism; it does not however foreshadow a key finding on which this invention is based, viz. that a direct ligand to metal charge transfer mechanism can be utilised which is far more efficient in terms of energy transfer and which is far more specific in the production of the luminescence signal.

Several other related approaches to DNA recognition have been reported. Hélène and colleagues use a probe DNA strand to which is attached a fluorescent intercalating handle [PCT Int. App. WO88,04301; C. Hélène and N. T. Thuong, Pont. Acad. Sci. Scripta Varia, 1988, 70, 205–222]. On hybridising this handle can intercalate into the adjacent duplex and this changes the fluorescent characteristics. However this method suffers from lack of sensitivity since the unhybridised probe molecules retain an incipient fluorescence characteristic and this adds to the problems of background fluorescence interference. Barton et al. have used a similar approach to that of Hélène but use complexes of ruthenium as intercalators in place of organic fluorophores [PCT Int. App. WO-88/04301; see J. K. Barton et al., Biochemistry, 1992, 31, 10809–10816]. The advantage of these latter complexes is that the efficiency of luminescence is low in water but high in an intercalating environment. No synergy is involved in the latter case and hence their selectivity is not particularly high since any intercalation event leads to luminescence.

Yet another method (European Patent Application 0382433A2) utilises a polynucleotide probe labelled with a fluorescent reagent and uses the phenomenon of fluorescence polarisation to study the binding of the probe to the target polynucleotide.

As indicated in the above examples, fluorescence detection is widely used in hybridisation assays. In fluorescence spectroscopy the substance to be determined, which is present in a liquid or a solid phase, is subjected to radiation from a source of known spectral distribution, for instance light with a limited bandwidth. The fluorescent radiation generated has a longer wavelength than the exciting radiation and this radiation is specific for the substance to be determined. The measurement of the intensity of the fluorescent radiation constitutes a quantification of the substance to be determined. Fluorescent moieties attached to a polynucleotide are most efficient when they have a high intensity, a relatively long emission wavelength (more than 500 nm), a high Stoke's shift and the ability to be bound to the polynucleotide without affecting its hybridisation capabilities. Aromatic agents used in biological systems that give a strong fluorescence are well known.

Fluorescence is generally measured with a spectrofluorimeter. A disadvantage of current methods for detecting signalling groups with spectrofluorimeters is that the detection sensitivity is limited because of interfering fluorescence or noise in the exciting and detecting systems that increases the background. The background is also affected by a heavy scattering which gives rise to an interference, especially when aromatic organic agents with a small Stoke's shift (less than 50 nm) are used.

Several approaches have been described that attempt to overcome the background problem with fluorescence detection. One approach [U.S. Pat. No. 4,058,732] measures delayed luminescence, using a signalling group that possesses a luminescence having a much longer duration than that of the fluorescence of the noise and background sources. A laser pulse is used to excite the sample and the detection of the luminescence from the signalling group is only measured after a sufficiently long time when the fluorescence from the noise and background sources have decayed. This method has drawbacks in that, hitherto, it is not readily adaptable to commercial use and is not amenable for a homogeneous assay.

A second approach [U.S. Pat. No. 4,374,120] involves a method for determining the presence of an antigen by first attaching a ligand to an antibody, complexing a lanthanide metal to the ligand and then binding the labelled antibody to the antigen. The complex has to be separated (a heterogeneous assay) from uncomplexed antibody and the antigen-antibody complex then measured by transferring the lanthanide ion to a second photosensitising ligand. Estimation of the amount of lanthanide ion is achieved by radiating to excite the second ligand; this then transfers the energy to the chelated metal which emits radiation at a longer wavelength and for a longer time period than the noise sources. A drawback in this method is that it cannot be used for a homogeneous assay as well as requiring several steps.

The present invention concerns a method for the detection and determination of an analyte, such as a polynucleotide strand DNA, by means of a direct ligand-metal energy transfer system that results in the emission of a characteristic, delayed luminescence emission.

Excitation of a sensitiser directly chelated to a lanthanide ion, such as europium (III), is followed by the ligand-metal energy transfer. Luminescence from the metal ion is characterised by a long lifetime, which can be measured after decay of background fluorescence signals and the light emission signals the presence of the analyte.

It is an object of this invention to provide a method for detecting an analyte by complexing it to a binding entity to which is attached one partner of an energy transfer system, for example a lanthanide chelating group, wherein the formation of the complex allows for the localisation of a sensitising entity, which behaves as the first partner of the energy transfer system, within a specific, binding distance of the second partner so that the first and second components form a closed chelated system around a lanthanide ion and, as a consequence, energy absorbed by the first component can be directly used to excite the chelated lanthanide ion. It is a requirement of the system that the waveband of the exciting radiation is substantially absorbed by the first partner of the energy transfer system and that the light emitted by the second partner, the excited lanthanide ion, is of longer wavelength than that used in the excitation step and that the duration of the emission is preferably substantially greater duration than that of any background fluorescence or noise generated by the irradiation process.

The invention also comprises a method for detecting an analyte by complexing it to a binding entity to which is attached the first partner of an energy transfer system, for example a sensitising entity, wherein the formation of the complex allows for the localisation of the lanthanide chelating group, which behaves as the second partner of the energy transfer system, within a specific binding distance of the first partner so that the first and second components form a closed chelated system around a lanthanide ion and, as a consequence, energy absorbed by the first component can be directly used to excite the chelated lanthanide ion. It is a requirement of this system that the waveband of the exciting radiation is only substantially absorbed by the first partner of the ligand to metal energy transfer system and that the light emitted by the second partner, the excited lanthanide ion, is of longer wavelength than that used in the excitation step and that preferably the lifetime of the emission is of substantially greater duration than that of any background fluorescence or noise generated by the irradiation process.

This invention further provides a method for detecting the presence of a target polynucleotide in solution by hybridising it to a polynucleotide probe to which is attached either the first or second component of a ligand-to-metal energy transfer system, comprising of a complexed lanthanide ion and a complexing sensitiser, to form a hybrid such that the second component of the energy transfer system may then be localised, either by intercalation or groove binding, within a specific binding distance of the first component to form a closed chelated system around the lanthanide ion and, as a consequence, energy absorbed by the first component can be directly used to excite the chelated lanthanide ion.

The invention also comprises a method for detecting the presence of a target polynucleotide by fixing the target polynucleotide to a support, contacting the target polynucleotide with a solution containing a polynucleotide probe to which is attached either the first or second component of an energy transfer system, comprising of a complexed lanthanide ion and a complexing sensitiser, to form a hybrid such that the other component of the ligand-to-metal energy transfer system may then be localised, either by intercalation or groove binding, within a specific binding distance of the first component to form a closed chelated system around the lanthanide ion and, as a consequence, energy absorbed by the first component can be directly used to excite the chelated lanthanide ion.

This invention further includes a method for detecting the presence of a target polynucleotide by fixing to a support a polynucleotide probe, to which is attached either the first or second component of an energy transfer system, comprising of a complexed lanthanide and a complexing sensitiser, contacting the probe with a solution containing the target polynucleotide to form a hybrid such that the other component of the energy transfer system may be localised, either by intercalation or groove binding, within a specific binding distance of the first component to form a closed chelated system around the lanthanide ion and, as a consequence, energy absorbed by the first component can be directly used to excite the lanthanide ion.

In these assay systems the probe polynucleotide can either be completely complementary to the polynucleotide sequence in the target analyte, in which case a high level luminescence response can be obtained, or a probe polynucleotide containing one or more mismatched bases as against the target sequence, in which case a reduced luminescence signal may be obtained, given appropriate polynucleotide design. In this manner one can search for the occurrence of and site of a mutation (mutations) in a target polynucleotide strand.

The components of the energy transfer system are a light absorbing moiety which can act as a sensitiser. Mechanisms for such energy transfer are well documented. Singlet-singlet energy transfer can occur either by direct contact between species or by Förster energy transfer processes in which the exchange of energy can occur through space over distances up to 30 nm. Triplet energy transfer is more efficient by direct contact, either by collision or by holding the partners adjacent to one another, as in metal complexes, for example by ligand-to-metal energy transfer processes. The acceptor can be an aromatic agent or a lanthanide metal. The latter process of energy transfer using a lanthanide metal as the acceptor is utilised in this invention. One of the drawbacks with many energy transfer signalling systems is the fact that the resulting signal is emitted with a short lifetime (fluorescence) and has to be collected at the same time as background signals, the consequence being a loss of sensitivity and selectivity. A method to overcome this involves the use of emitters with a long life-time, as in delayed fluorescence and phosphorescence (delayed luminescence). For such probe systems, the collection of emitted photons can be delayed, until the fast background emission has faded, before collecting the delayed luminescence signal, a process called gating. Such a procedure avoids the problems associated with background fluorescence and noise.

DETAILED DESCRIPTION OF THE INVENTION

1. General Description

This invention discloses a homogeneous assay for determining the presence of a polynucleotide analyte. Homogeneous solutions include any solution having solutes in the liquid phase. This also includes suspensions with fine suspensions or colloids or related mixtures which are sufficiently transparent or non-scattering to enable luminescence measurements to be made. The homogeneous assay permits the detection of the analyte by a direct metal-to-ligand energy transfer process. The assay involves hybridising the analyte with a complementary probe polynucleotide and addition of an intercalating agent to which is attached one partner of the energy transfer components. There is no need to remove unbound binding probe or unbound intercalating agent from the assay medium before detection can be achieved.

In some embodiments of the assay, all of the components are dissolved in a solution (liquid phase). In other embodiments, one, or more of the components are fixed to a solid support.

The energy transfer system comprises two parts, a chelating ligand, specific for a lanthanide ion, such as the europium (III) ion and to which the ligand is strongly bound in the range of pH values used in the assay. The ligand is selected such that the coordination sites around the lanthanide ion are not completely occupied. The second component of the energy transfer system is a sensitising ligand, that can also bind to the lanthanide ion, whilst the latter is still bound to the other chelating ligand. The sensitising ligand consists of an aromatic group that is capable of absorbing light in order to produce an excited state. The energy of this excited state is then transferred to the lanthanide ion. It is a key requirement of this invention that the transfer of excited state energy can only occur when the sensitiser and the chelated lanthanide ion are in close proximity, such as in direct contact by ligation. Energy absorbed by the sensitiser in this two-component complex (ligated europium and sensitiser) can be transmitted by specific, local, ligand-to-metal energy transfer resulting in the formation of an excited state of the lanthanide ion. This excited lanthanide ion may emit luminescence of a longer wavelength than that absorbed by the sensitiser and, in addition, the emitted fluorescence is of substantially longer duration than that of fluorescence emitted by the sensitiser or other background fluorescence. The presence of this delayed luminescence indicates the presence of the analyte.

The method is applicable to the detection of polynucleotides and can be carried out in a one phase system, in a homogeneous solution assay, or in a two phase system, i.e. in a solution over a solid support. The detection is carried out by forming a hybridised complex between the target polynucleotide and a complementary probe polynucleotide to which is affixed one of the components of the energy transfer system. The point of attachment of the energy transfer component is such that it does not interfere with the complementarity between the target polynucleotide and the complementary probe. The second component of the energy transfer system is linked to a duplex binder such as an intercalating agent or groove binder. The second component is such that, only after hybridisation between the probe polynucleotide and the target polynucleotide can, for example either the intercalating agent insert into the so-formed duplex strand of polynucleotides or groove binding occur. For example, the intercalation allows the second component of the energy transfer to approach the first component. Since intercalation is a reversible process, it is believed that the agent will move between the various base pairs of the duplex until it is within binding distance of the other component. This approach may also be aided by direct ligation of the sensitising ligand to the chelated lanthanide ion; when this ligation has occurred at the targeted analyte efficient energy transfer between the sensitising ligand and the chelated lanthanide ion can take place and thus delayed luminescence be observed.

A number of embodiments are described below by way of Example.

1. The analyte is a target polynucleotide and the binding entity comprises a complementary probe polynucleotide to which is attached a chelated lanthanide ion. The sensitising ligand is either a duplex binder or is attached to an duplex binder. All the components are dissolved in the liquid phase. By way of illustration of this embodiment see FIG. 1.

2. The analyte is a target polynucleotide and the binding entity comprises a complementary probe polynucleotide to which is attached a sensitising ligand. The chelated lanthanide ion is attached to a duplex binder. All the components are dissolved in the liquid phase.

3. The analyte is a target polynucleotide and is fixed onto a solid support. The binding entity comprises a complementary probe polynucleotide to which is attached a chelated lanthanide ion. The sensitising ligand is either a duplex binder, or is attached to a duplex binder. Both components of the energy transfer system are initially dissolved in the liquid phase.

4. The analyte is a target polynucleotide and is fixed onto a solid support. The binding entity comprises a complementary probe polynucleotide to which is attached a sensitising ligand. The chelated lanthanide ion is attached to a duplex binder. Both components of the energy transfer system are initially dissolved in the liquid phase.

5. The binding entity, comprising a complementary probe polynucleotide to which is attached a chelated lanthanide ion, is fixed onto a solid support. The analyte is a target polynucleotide and the sensitising ligand is either a duplex binder, or is attached to a duplex binder. Both the analyte and the sensitising ligand are initially dissolved in the liquid phase.

6. The binding entity comprising a complementary probe polynucleotide to which is attached a sensitising ligand is fixed onto a solid support. The analyte is a target polynucleotide and the chelated lanthanide ion is attached to a duplex binder. Both the analyte and the intercalating agent are initially dissolved in the liquid phase.

The duplex binder is an intercalator, groove binder or any other moiety that binds to duplex but not single-stranded nucleic acid. Preferably, the duplex binder is an intercalator.

Whilst we do not wish to be bound by theoretical considerations, the method of the assay involves irradiating a sensitiser which is in direct association with a lanthanide ion via chelation. This forms an excited state species of higher energy than that of the ground state. Providing the resulting excited state has enough energy this can be transferred directly to the lanthanide ion, the advantage of the direct association resulting in a very efficient energy transfer process; through space energy transfer processes are generally much less efficient. The energy transfer results in the formation of an excited state lanthanide ion which can return to the ground state by emission of light energy. Since the excited state to ground state transformation of the lanthanide ions involve inner shell electrons, the pattern of light emission is very characteristic, in which the wavelength of the emissions are not greatly influenced by the local environment. The wavelength of emission is far removed (a large Stoke's shift) from that of the initial absorption process. Furthermore, the nature of the emission process results in a long lifetime (delayed luminescence) which allows for the measurement of the emitted light after a short time interval, during which any fluorescence emission from any background and noise processes has decayed. Important limitations are that the binding of the chelating ligand for the lanthanide ion should be high so that, at the concentrations and pH employed for the assay, no, or only a very limited amount of, dissociation of the ligand for the lanthanide occurs. Furthermore, the binding constant of the sensitising ligand for the chelated lanthanide ion should be such that, at the concentrations used for the assay, little random binding between these energy transfer agents occurs in the absence of the target polynucleotide, since such random binding will lead to energy transfer and hence the emission of a background delayed luminescence signal.

By way of illustration, an example of a one phase assay, where the analyte is a polynucleotide in solution, is the addition of the complementary polynucleotide probe, to which is attached the chelated lanthanide ion, together with a duplex binder to which is attached a sensitising ligand. The concentration of the polynucleotide probe and the sensitising ligand is such that little random association of these components occurs. The target polynucleotide and the probe polynucleotide components are then hybridised to form a double strand of polynucleotide. The presence of the doubly stranded polynucleotide allows for intercalation by the sensitising reagent. The association constant for intercalation localises the sensitiser at the doubly stranded nucleic acid and thus the local concentration of the intercalator is increased. Intercalation is a dynamic association—dissociation process such that movement of the intercalating agent between different intercalation sites along the matched doubly stranded polynucleotide sequence can occur. When in close proximity to the lanthanide chelate a further binding to the metal ion by the chelating ligand can occur, thus helping to fix the components in a cooperative manner. Only when all three components, the polynucleotide target, the polynucleotide probe and the sensitiser come together in this cooperative way does irradiation of the sensitiser give the delayed luminescence signal, indicating a positive identification of the target; the signal intensity can be used to quantify the analyte. For polynucleotide probes that do not find a complementary polynucleotide sequence, no hybridisation can occur and hence no cooperative enhancement of the delayed luminescence would be observed.

An example of the two-phase assay would be where the polynucleotide target is first bound to a solid support, such as a sheet of nitrocellulose. The assay would then be carried out by adding to the supported polynucleotide a solution of the two reagents, the probe polynucleotide to which is attached, for example, the chelated lanthanide sensitiser, and the intercalating reagent to which is attached the sensitising ligand. The polynucleotides are allowed to hybridise. After equilibration any excess of reagents are washed off and the bound complex then irradiated with light and the delayed luminescence measured. If no target polynucleotide were present no intercalation could take place and hence no sensitisation of the lanthanide ion would be observed, i.e. no delayed luminescence would occur.

For assays involving a polynucleotide target a complete base sequence match of the analyte to the probe is not always essential. Thus, by way of illustration, one could analyse for a target bearing a base mutation (or mutations) in the region complementary to the probe. This would cause a mismatch at this location, with the consequent formation of a 'bubble' in the resulting polynucleotide duplex. From theoretical considerations and/or by experimentation it is possible to design the probe such that this bubble is located in the region where the duplex binder-sensitizer would bind in the complex. Because intercalation, or groove binding, would be weaker in this region, one would produce less luminescent signal than that for the match. By comparing this with the intensity of the matching probe one would gain information on the presence and location of the mutation(s). A further way of detecting mutations is by use of allele-specific probes designed such that the mutation causes the probe not to hybridise, whilst the absence of the mutation causes hybridisation and a luminescent signal. Heterozygotes would give a reduced signal.

In a particularly convenient aspect the method of the invention is a homogeneous, one-step assay using a PCR product as target polynucleotide, one or more assay components such as the complementary probe polynucleotide being present at the the start of the PCR amplification. Preferably all of the assay components are present. That is to say the method comprises a self-contained amplification and detection system. A particular advantage is that contamination may be avoided, for example since after amplification no further reagents are required and therefore there is no need to unseal the reaction vessel. Examples of other convenient systems will be apparent to the molecular biologist of ordinary skill.

Suitable hybridisation conditions for nucleic acid hybridisation may be determined by routine experimentation. Convenient conditions are outlined in "Hybridisation—A Practical Approach" edited by B. D. Hames and S. J. Higgins (IRL Press, Oxford, 1988)

2. Description of the Polynucleotide Probe Entity

This is comprised of two segments, the polynucleotide recognition segment and one of the signalling components. The recognition segment comprises a polynucleotide probe that recognises the chosen target polynucleotide. The polynucleotide probe can undergo hybridisation with a complementary sequence of bases in the polynucleotide target to be detected. The sequence of the probe polynucleotide should be at least six bases, preferably between six to fifty and optimally between twelve and thirty, in order to impart specificity to the probe and to ensure secure binding between it and its target. However, such a base sequence need not be a single continuous complementary polynucleotide sequence but can be comprised of two or more individual complementary sequences interrupted by non-complementary sequences. In addition, the complementary region of the probe can be flanked at the 3'- and 5'-termini by non-complementary sequences, such as either those comprising the DNA or RNA vector into which the homologous sequence has been inserted for propagation or a variety of blocking groups to prevent, for example, recognition in transcription processes. In either instance, the probe as presented as an analytical reagent will exhibit detectable hybridisation at one or more points with the sample polynucleotides of interest.

Alternatively the polynucleotide recognition segment is comprised of two or more polynucleotide sequences to be joined for example by ligation or cleaved, for example by restriction enzyme(s), after hybridisation to the target. The target sequence of interest may be complementary to one or more of the polynucleotide sequences.

It will be understood that the signalling components may be attached to the above polynucleotide sequences in a number of ways. The components may be attached via the same polynucleotide sequences or alternatively via adjacent polynucleotide sequences. Thus by way of example, the chelating ligand and the sensitising ligand may be attached to separate polynucleotide sequences. The polynucleotide sequences may be contiguous or be separated by gaps to be "filled in" using appropriate dNTPs. The lengths of the polynucleotide sequences will be determined by practical consideration. In general these will comprise at least eight nucleotides.

2.1. The polynucleotide segment

Methods for preparing the polynucleotide segment of the probe that is substantially complementary to a target polynucleotide are well known and routine in the art. One method involves recombinant DNA and another cloning, as detailed in 'M13 Cloning and Sequencing Handbook', published by Amersham International (1983) and in 'Molecular Cloning', by T. Maniatis, E. F. Fritsch and J. Sambrook, published by Cold Spring Harbor Laboratory (1982). Use of the polymerase chain reaction (PCR) can also be made to amplify target polynucleotide chains (K. Kleppe, et al. J. Mol. Biol., 1971, 56, 341–346; 'PCR Technology', ed by H. A. Erlich, Stockton Press, New York, 1989. Specific polynucleotides can also be prepared by using a DNA Synthesiser, such as the model 380B produced by Applied Biosystems, Foster City, Calif. or the Cyclone series of synthesisers supplied by Millipore Corporation, U.S.A. It will be understood that the term polynucleotide includes DNA, RNA and analogues thereof which are able specifically to hybridise to the target.

The signalling component is a segment of the polynucleotide probe that is involved in the energy transfer process leading to delayed luminescence. The signalling segment is attached to the polynucleotide recognition segment either directly or through a linker arm. The signalling segment may be either the lanthanide chelator or the sensitising ligand.

The delayed luminescence should only occur when the polynucleotide segment of the polynucleotide probe is hybridised with the target polynucleotide. The delayed luminescence should not occur in the presence of hybrids if none of the hybrid strands is that of the target polynucleotide. The target polynucleotide, to which the polynucleotide segment of the polynucleotide probe hybridises, must be one originating from the sample. Thus, the polynucleotide probe must be presented to the target polynucleotide sample in single stranded form and should not have the ability to form a doubly stranded hybrid with itself. If the latter situation prevailed the doubly stranded probe polynucleotide will interact with the intercalating agent such that the collaborative combination of the sensitiser with the chelated lanthanide ion could occur, thus leading to the observation of delayed luminescence. This will produce a false positive result. The formation of hairpin loops in the polynucleotide probe can also result in the production of a false positive result in the presence of the intercalating agent. Selection of the probe sequence must take these possibilities into account but can be easily checked for by carrying out the appropriate control measurements. The possible formation of doubly stranded material by the interaction of the probe polynucleotide with itself may be minimised by careful selection of the base sequence to be searched for and by normally using polynucleotide probes not longer than about 30 base sequences.

2.2. Attachment of the signalling segment

The signalling segment of the polynucleotide probe may be either a lanthanide chelating group, which binds the metal ion strongly and essentially irreversibly under the conditions used throughout the assay protocol, or a sensitising ligand. This may be linked directly to the polynucleotide segment or via a covalently bound linker arm. The point of attachment to the polynucleotide may either be to a nucleic acid base group, a sugar group or a phosphate group. The base group may be either a pyrimidine or purine unit. The attachment of the linker arm should preferably be such that it does not interfere with the Watson-Crick pairing of complementary bases. Suitable positions are, for example, positions 5 and 6 of uracil, positions 5 and 6 or the exocyclic 4-amino group of cytosine, positions 7 and 8 of deazapurine, position 8 of guanine and positions 8 and the exocyclic 6-amino group of adenine. A preferred linker arm for attachment to the base moiety is allylamine [see European Patent No. 063,879].

Linkage through a hydroxyl group can be achieved, for example by an ester or ether link to the 3'- or the 5'-terminal hydroxyl group of deoxyribose. Linkage to a phosphate group can be by means of an alkyl phosphate ester link, either to the 3'- or the 5'-terminal positions of the polynucleotide. The linker arm should be chosen so that it is stable under the conditions used in the assay protocol. The method for attaching the linker arm should be any that does not result in the modification or blocking of the functional groups of the bases required for hybridisation or the cleavage of the base from the sugar. Conveniently the 5' and/or 3' termini, preferably the 5' terminus, are used for attachment.

2.3. The linker arm

The linker arm comprises a group of atoms joining the polynucleotide recognition segment to the chelator-metal complex or the sensitiser. The linker arm can be joined to the polynucleotide recognition segment by any number of methods. The linker arm must have a first functional group by means of which it can be attached to the recognition segment and a second functional group by means of which it can be attached to either the lanthanide metal chelator or the sensitising ligand. The linker arm can be attached for example by means of a carbon-carbon single bond, carbon-carbon double bond, carbon-carbon triple bond, carbon-nitrogen single bond, carbon-nitrogen double bond, carbon-oxygen single bond, carbon-sulphur single bond, carbon-silicon single bond, sulphur-nitrogen bond, sulphur-oxygen bond, phosphorous-oxygen bond, or phosphorous-nitrogen bond.

Suitable functional groups include but are not limited to, hydroxyl groups, amino groups, thio groups, alkyl sulphates, and halides. It is not necessary that the linker arm be attached to the polynucleotide recognition segment as one fragment.

2.4. Attachment of the linker to the polynucleotide recognition segment

Where the linker is attached to the 5' or 3' terminus of the polynucleotide, convenient linkages include phosphate, carboxy or ether linkages, particularly phosphate linkages. Suitable phosphate linkers include aminoalkylphosphoryl groups, especially those comprising a C1–12 alkyl chain, especially a C6 alkyl chain. These linkers may be readily attached to synthetic oligonucleotides during solid-phase synthesis, see for example S. Agrawal et al, Nucleic Acids Research, 1986, 14, 6227 and WO-88/02004 (Applied Biosystems). The amino group may then be used for the attachment of the chelator-metal complex or the sensitizer. Alternatively the linker can be constructed by attaching a first fragment to the recognition segment, followed by the attachment of a second fragment to the first fragment.

Examples of suitable first fragments include:
—NH—CH$_2$—CH═CH—, SH—CH$_2$—CH$_2$—CH═CH—, —NH—CH$_2$—CH$_2$—O—CH$_2$—CH═CH—, —(CH2)$_n$—O— where n is an integer from 1 to 20.

Examples of suitable second fragments include those introduced by means of:

| | | |
|---|---|---|
| N—O—CO—R; N-hydroxysuccinimide esters | R—C(═NH)—OR; imidates | R—CO—O—CO—R; anhydrides |
| R—N═C═S; isothiocyanates | R—CO—SR and thioestets | R—(C═S)—SR dithioesters |

Second fragments or the chelator or the sensitizer may be introduced via the amine reactive functions, for example: R—COO—Su (wherein Su represents a succinimidyl group), R—(C═NH)—OR, R—COO—CO—R, R—N=C=S and R—CS—SR or by thiol reactive functions —R—O—C(=O)—CH$_2$—X (wherein X=a halide group), R—Ma (wherein Ma represents a maleimido group), R—S—S—Y (wherein Y is preferably an electron withdrawing group such as a pyridyl group). In all the above fragments R represents a linker group as hereinbefore defined.

Other general methods for attaching a linker arm onto a polynucleotide base are discussed in J. L. Ruth and D. E. Bergstrom, J. Org. Chem., 1978, 43, 2870; D. E. Bergstrom and M. K. Ogawa, J. Amer. Chem. Soc., 1978, 10, 8106; and C. F. Bigge, P. Kalaritis, J. R. Deck and M. P. Mertes, J. Amer. Chem. Soc., 1980, 102, 2033. One preferred method is the one disclosed in detail in European Patent Application No. 063,879, which is hereby incorporated by reference. The method involves reacting a linker arm or a linker arm fragment containing an alpha-vinyl group with a mercurated base in the presence of K$_2$PdCl$_4$, wherein the mercury is bound as Hg+ to the position of the base which is to react with the linker arm.

There are no particular size or content limitations for the linker arm provided that it can fulfil its stated purpose. The linker arm can contain from about two carbons to any number of carbons. The linker arm can contain heteroatoms and unsaturations, The linker arm can comprise aliphatic, alicyclic, aromatic or heterocyclic groups. It conveniently comprises —(CH$_2$)$_n$—. It may however include other groups such as —O—, —CHOH—, —COO—, and —CH$_2$CH$_2$—O— which help maintain water solubility. When the linker is —(CH$_2$)$_n$— and n is eight or more then it should preferably not comprise methylenes alone but include other groups as described above, or be introduced via two fragments as described above.

Attachment of the linker arm to the sugar group of a polynucleotide can be by means of a Schiff base to the 1'-aldehyde following depurination or depyrimidation of preselected bases or it can be to the 2'-hydroxy in the case when the sugar is ribose. Attachment of a linker arm to the phosphate moiety can be by alkylation of the phosphate group, see U.S. Pat. No. 4,469,863, which is hereby incorporated by reference.

When the linker arm is attached to the base group, it is preferable to attach it to the base before formation of the polynucleotide. This is because the reaction conditions that may be required to attach the linker arm to the base may cause undesirable side reactions to a polynucleotide. Furthermore, attachment at the polynucleotide level may give inconsistent and irreproducible yields. Attachment at the nucleoside or nucleotide level permits the modified nucleoside or nucleotide to first be purified and then to be incorporated into a polynucleotide. The incorporation can either be by cloning, for example, in an M13 vector, or by synthesis in a polynucleotide synthesiser instrument as described above.

For incorporation by a M13 vector, the modified nucleotide must be a relatively efficient substrate for the commonly studied nucleic acid polymerases. Thus, the linker arm should not sterically interfere either with the active site on the enzyme or with the complementary base pairing of the modified nucleotide. Substitution at positions that alter the normal 'anti' nucleoside conformation should also be avoided since such conformational changes usually render the modified nucleotide a poor substrate for the polymerase enzymes.

When the linker arm is attached to the 1'-aldehyde of the sugar, the linker arm must be attached following the formation of the polynucleotide portion of the polynucleotide probe. This is because attachment of the sugar requires a free aldehyde at the 1'-position of the sugar. The free aldehyde is formed by depurination or depyrimidation. A group comprising a sugar and a phosphate without a base is not a substrate for the polymerase enzymes. Thus the linker arm must be attached by first selectively depurinating or depyrimidinating the desired polynucleotide sequence and then attaching the linker arm to the sugar by means of the aldehyde. When the linker arm is attached to the 2'-hydroxy group of a ribose sugar, the linker arm can be attached at the nucleoside, nucleotide or polynucleotide level. This is because nucleotides modified by a linker arm can be incorporated into a polynucleotide by means of a polynucleotide synthesiser instrument. When the linker arm is attached to the phosphate, the linker arm is preferably attached at the nucleoside or nucleotide level so that the attachment is not at positions other than at a phosphate. Phosphoramidite technology may be used in a nucleic acid synthesiser to incorporate the linker to the 5' or 3' end of the polynucleotide.

2.5. Attachment of the Chelator to the Linker

A chelator is a group which can sequester and bind a metallic cation. The chelator has two or more functional groups which interact non-covalently with the metal. The attachment of metal chelating groups to polynucleotides is known in the art. [See European Patent Nos. 097,373, 150,844 and 157,788, which are hereby incorporated by reference.] The chelator acts to shield the lanthanide from water. It is a key requirement in this invention that the chelator does not saturate all the possible binding sites around the lanthanide ion since space must become available around the ion to accommodate the sensitising ligand.

Examples of chelators, not meant for limitation, are ethylenediaminetetraacetic acid (EDTA), diethylenetriaminepentaacetic acid (DTPA); trans-1,2-diaminocyclohexanetetraacetic acid (DCTA); 1,4,10-trioxa-7,13-diazacyclopentadecane-7,13-diacetic acid and polycyclic aza-crown systems such as bicyclo[5.5.2]1,4,7,10-tetraazacyclotetradecane-4,10-diacetic acid. Modified derivatives of the above, such as 1-phenylethylenediaminetetraacetic acid, allow for sites where linking groups can be placed in the aromatic ring, such as the diazonium or isothiocyanate derivatives.

Other examples of suitable chelators include polyfunctional compounds such as crown ethers, caged compounds, clathrates with suitable donor groups to bind the lanthanide. These groups will conveniently include nitrogens, oxygens, for example on ethers or carboxylic acid groups. The selection of a suitable chelators will be apparent to the chemist or ordinary skill. Other chelators and the factors influencing their effectiveness are reviewed in 'Cation Binding by Macrocycles' ed. Y. Inoue and G. W. Gokel, pp 203–251 by T. M. Fyles published by Marcel Dekker, New York 1990. A further review is provided by Arnaud-Neu in Chemical Society Reviews, 1994, 23, 4, 235–241; this describes inter alia the use of coronands, cryptands, calixarenes and modified versions thereof to form stable lanthanide complexes where not all available sites on the lanthanide ion are occupied.

The chelator can be attached to its linker by a number of groups. Examples, not intended for limitation, are: —O—, —NH.CO—, —NH.C(NH)—, —NH.C(S)—, —N=N—, —NH.SO2—, —S—, —O.PO2—, —O.SO2—, —NH—N=N—, —NH—CH2—, —CH2.NH—, —NR—, —O.CH2—, —O.CO—, —NH.CO.CH2.S—, —NH.CO.CH2.NH—, —O.CH2.CH2.O—, —O.CO.CH2—, —S.CH2—, and —O.CO.NH—.

Alternatively one of the carboxyl groups of a chelator as outlined above may be used for attachment of the linker. The use of anhydrides, for example EDTA anhydride, is particularly convenient. It will be appreciated that in certain circumstances the chelator may contain groups which act as sensitisers for the metal.

Varying conditions can be used for attaching a chelator to a linker arm. Generally any pH range from about 4 to about 10, preferably from about 5 to about 8, any temperature from about 20° C. to about 100° C., any solvent, preferably water, and any buffer or catalyst can be used as long as the pH, temperature, solvent or buffer does not modify any of the groups or moieties of the polynucleotide. Thus, for example, reagents or conditions that can depurinate or deaminate the polynucleotide should be avoided. There are also relatively few limitations as to reaction times. The optimum pH, temperature, solvent or reaction time for attaching the chelator to a linker arm will depend on the linker arm, the chelator, and the functionalities to be reacted and may be determined by the scientist of ordinary skill.

The stoichiometries of the reactants required for these linking reactions vary widely. Generally, an excess of the component that is more easily prepared will be used for the attachment of the chelator to the polynucleotide. Again, the amounts will vary depending upon the reaction conditions, the chelator, the linker arm and their reacting functional groups.

The chelator can be attached to the linker arm either after incorporation of the linker arm to the polynucleotide or before incorporation of the linker arm into the nucleotide. The only limitation is that the chelator cannot be attached before incorporation if it interferes with polynucleotide synthesis. The binding entity can comprise one chelator or more than one chelator. For the polynucleotide recognition segment the chelator can be attached at terminal positions or at non-terminal positions of the polynucleotide probe. The greater the number of chelators the more sensitive the binding entity will be. However, the chelators should not be present in such numbers that effective complexing of the analyte to the binding entity is substantially prevented. The number of chelators that can be attached will depend on the composition, the size and the length of the recognition segment.

2.6. Attachment of the metal

Of the lanthanide metal chelates those of terbium, europium, samarium and dysposium can exhibit long-lived luminescence of up to the millisecond range. Terbium emits in the range 480 to 630 nm and europium in the range 580 to 700 nm. Europium is the preferred metal. Neither of these ions show strong absorbance (extinction coefficients) in aqueous solution and chelates with non-sensitising ligands, for example EDTA, also show very low extinction coefficients, the weak absorption occurring in discrete regions, of 270–320 nm and about 488 nm for terbium and of 320–360 nm and about 580 nm for europium. The excited state of these metals can be reached by use of energy transfer from suitable sensitisers. Singlet energy sensitisers, employing through space Förster energy exchange mechanisms, are inefficient since it is believed that the excited state of these lanthanide ions are formally forbidden and the processes require triplet state sensitisation. Triplet state sensitisers do not efficiently transfer energy through space, requiring close contact, such as collisions in order to transfer their energy. The excitation process can be achieved efficiently by use of triplet sensitisers which can act as ligands, i.e. they are always held in close contact with the metal ion. The metal ion can be chelated to the chelator by stirring a solution of the latter in a solvent with a solution of the metal salt, such as a halide or nitrate salt in the range of pH 5 to 10, preferably between 6 and 8. The formation of the chelated lanthanide may be slow and can take several hours. However, once formed because the binding constants are high, dissociation is extremely slow and the process is essentially irreversible within the range of pH 5 to 10.

As an alternative to the attachment of the chelator to the linker one can attach the sensitiser, as detailed below.

3. Description of the Sensitiser

The sensitiser is the antenna for the energy transfer process. It acts to efficiently pass on its excited state energy to the lanthanide when they are in close proximity, as accomplished by ligation. The sensitiser can be any of a range of possible organic, aromatic or heteroaromatic systems that can act as triplet sensitisers. A key requirement in this invention is that the systems can act as ligands for the lanthanide ion without displacing the chelating group around the ion; both the sensitiser and the chelator must be able to reach and bind to the lanthanide ion at the same time and when in the presence of the analyte. Suitable ligand sensitisers include but are not limited to beta-diketones of the general formula I, where R1, R2, R3=alkyl, heterocyclic, aromatic or heteroaromatic groups, ethers, esters, amides, etc.

Heterocyclic systems include but are not limited to substituted dipyridyl compounds of the general formula II and phenanthrolines of the general formula III where R1, R2=a chelating group, such as —CO2H, —CO.NHR, —CO.NR2, —CO.NR1,R2, —CO.NH.OH, —CH2CO2H, —CH2.CO.NHOH, —CH2PO.(OH)2, —CH2.PO(R)OH, —CH2OH, —CH2SH, —PO(OH)2, —PO(R)OH, —CH2N(CH2.CO2H)2. Other convenient heterocyclic systems have been described in the literature and will be apparent to the scientist of ordinary skill.

The sensitiser may also bear a linker (R3); the linker arm comprises the group of atoms joining the sensitiser to either the probe polynucleotide or the intercalator. The linker can be attached to the sensitiser by a number of groups. Examples of such groups, not intended for limitation are those detailed for the attachment of the linker to the chelator.

4. Description of the duplex binder

A number of aromatic agents or dyes are able to bind to double-stranded polynucleotide either by the process of intercalation, in which the agent inserts itself between adjacent sets of the hydrogen-bonded base pairs or by binding in either the major or minor grooves of the duplex. The double strand polynucleotide can be DNA—DNA, DNA—RNA or RNA—RNA.

A result of intercalation is the spreading of adjacent base pairs to about twice their normal separation distance, leading to an increase in molecular length of the duplex. Some unwinding of the double helix must also occur in order to accommodate the intercalator [see M. J. Waring and L. P. G. Wakelin, Nature, (London), 1974, 252, 653; L. P. G. Wakelin, Med. Chem. Rev., 1986, 6, 275.] Examples of intercalating agents, not intended for limitation, are acridine dyes, e.g. acridine orange and acriflavine, the phenanthridines, e.g. ethidium, anthracyclines, e.g. adriamycin, quinoxalones, e.g. dactinomycin, the phenazines, quinolines, anthracenes, furocoumarins, and phenothiazines.

The intercalators form reversible complexes with the duplex DNA, the rates of association and dissociation being fairly rapid and temperature dependent; the association constants being in the range of $10^4$–$10^8$ mol$^{-1}$, usually in the order of $10^6$ mol$^{-1}$. It is important that the rate of this process is fairly fast so that intercalation between different base pairs occurs until the agent is within reaching distance of the chelated lanthanide ion in order to form the active complex.

Example of groove binding agents, not intended for limitation, are the polypyrrole antibiotics netropsin and distamycin, the diamidines bevenil and hydroxystibamidine, Hoechst 33258, DAPI (4',6-diamidino-2-phenylindole), chromomycin, olivomycin, mithramycin and crystal violet.

The duplex binder is preferably attached to a linker; a linker arm comprises an atom or group of atoms joining the intercalator to either the sensitising ligand or the chelator. Examples of such groups but not intended for limitation are those detailed for the attachment of the linker to the chelator.

5. The Linked Duplex binder—Sensitiser

The intercalator linked sensitiser compounds described herein under the general formula (IV), where the component parts are described in sections 3 and 4 above, are new compounds and are claimed as part of this invention. Linkage of the duplex binder to the sensitizer/chelator is conveniently effected using a linker arm which will conveniently comprise —$(CH2)_n$— where n is between 2 and 20, preferably between 4 and 12. The linkage to the sensitiser or chelator and to the duplex binder will depend on the chemical nature of those moieties and any convenient means that preserves the function of those moieties may be employed. Such linkages will be apparent to a chemist of ordinary skill. Preferably the linkage will not contain bulky atom groupings. Preferably the linker in the vicinity of the duplex binder will not be hydrophilic and preferably will not contain negative charges.

6. The Analyte

The method of the invention can be used to detect a target polynucleotide, for example, from any convenient eukaryotic or prokaryotic species such as a microorganism, a plant cell or a mammalian cell. The microorganism can be a bacteria, fungus, virus or yeast. The target polynucleotide can be one that is unique for a particular pathogenic virus, one that is present in a mutated mammalian gene that results in the production of a non-naturally acting protein, or one that imparts resistance to a bacteria. It can also be a product polynucleotide arising from the amplification of a polynucleotide by use of the polymerase chain reaction, or as prepared by cloning methods. A particular product polynucleotide arises from the use of the polymerase chain reaction (PCR) as decribed for example in European Patent No. 0 201 184 or from the use of the Amplification Refractory Mutation System (ARMS) as claimed in European Patent No. 0 332 435 B1 (Zeneca Limited). Further product polynucleotides may be obtained by the use of Q-beta replicase as described in PCT patent application, publication no. WO-87/06270; by the use of the transcription-based nucleic acid amplification (TAS) of Siska Corporation as described in PCT patent application, publication no. WO-88/10315; by the use of single primer amplification (SPA) as described in European patent application, publication no. 0 469 755 (SYNTEX); by the use of sustained sequence replication (3SR); by the use of ligase chain reaction (LCR); or by the use of repair chain reaction (RCE).

PCR amplification and, for some applications ARMS amplification, is a preferred first step in the detection methods of the present invention.

The test sample to be assayed can be any medium of interest, and will usually be a liquid sample of medical, veterinary, environmental, nutritional, or industrial significance. Human and animal specimens and body fluids can be assayed by the present method, including urine, blood (serum or plasma), amniotic fluid, milk, cerebrospinal fluid, sputum, fecal matter, lung aspirates, throat swabs, genital swabs and exudates, rectal swabs, and nasopharyngeal aspirates. Where the test sample obtained from the patient or other source to be tested contains principally double stranded nucleic acids, such as contained in cells, the sample will be treated to denature the nucleic acids, and if necessary first release nucleic acids from cells. Denaturation of the nucleic acids is preferably accomplished by heating in boiling water or alkali treatment, e.g. 0.1M sodium hydroxide, which, if desired, can be simultaneously used to lyse cells. Also, release of nucleic acids can, for example, be obtained by mechanical disruption, (freeze/thaw, abrasion, sonication) physical/chemical disruption (detergents such as Triton, Tween, sodium dodecylate, alkali treatment, osmotic shock, or heat) or enzymic lysis (lysozyme, proteinase, pepsin). The resulting test medium will contain the nucleic acids in single stranded form which can then be assayed according to the present hybridisation method.

FIG. 1 illustrates the key parts of the invention as exemplified by use of an intercalator. It is a requirement that the links used do not interfere with the possibility of the sensitiser and chelator reaching each other. They should be selected such that their overall length is neither too long nor too short. Typically the number of atoms in each link should be between two to twenty atoms such that the combined length of the two links is between four and fourty atoms, optimally between ten and thirty atoms.

The test sample is conveniently obtained from target eukaryotic cells and comprises samples of genomic DNA and/or RNA for the analysis of, for example, inherited or acquired disease, the determination of identity including paternity, predisposition to disease or a particular condition; and population polymorphisms.

The invention is of particular use in HLA typing and the detection and/or diagnosis of cystic fibrosis, sickle cell anaemia and cancer.

7. Multiplex Testing

It will be appreciated that the methods of the invention may be used to detect more than one target polynucleotide simultaneously.

A convenient method comprises the use of one or more Förster energy transfer acceptor able to accept energy from the luminescent lanthanide complex of the invention. A number of different such acceptors that would emit light of a different wavelength are selected and used such that each energy transfer event was indicative of a different nucleic acid sequence. Luminescence energy transfer has been disclosed for the detection of DNA, see for example P. R. Selvin et al. J. Am. Chem. Soc. 116, 6029–6030 (1994). A number of variations using energy transfer acceptors are possible:

Variation 1: The energy transfer acceptor is coupled to the polynucleotide probe of the invention. Thus for multiple detection, each oligonucleotide probe, of varying sequence, emits light of a distinct wavelength which is indicative of the presence of the target nucleic acid complementary to that probe. Coupling of the energy transfer acceptor to the probe is at any convenient point that does not interefere with its function. Preferably it is positioned within the Ro value for the energy transfer pair selected. Conveniently, where the sensitisor or chelating ligand is positioned at one terminus of the polynucleotide, the energy transfer acceptor is attached to the opposite terminus. Alternatively it is attached to a base.

Variation 2: The energy transfer acceptor is coupled to a polynucleotide probe that has been selected to bind to the target nucleic acid adjacent to the polynucleotide bearing the sensitiser or chelating ligand. A signal is thus observed only when both polynucleotide probes are bound to the target nucleic acid. Again the attachment to the polynucleotide probe is at any convenient point that does not effect function and, together with the selection of the polynucleotide probe sequence, is selected such that a useful degree of energy transfer from the luminescent lanthanide complex takes place.

Variation 3. Variation 2 is employed but the adjacent polynucleotide probe bearing the energy transfer acceptor is an allele-specific probe. Thus the presence or absence of acceptor emission determines the presence or absence of a particular allele on the target DNA. A further use of this is in conjunction with a mismatched polynucleotide for the detection of phase of closely linked mutations, for example in the HLA locus. In this manner the wavelength of light emission will indicate the presence of one or both mutations.

The use of energy transfer acceptors is believed to have certain advantages which also apply to the detection of single nucleic acid sequences (non-multiplexed assays). For example the use of adjacent polynucleotide probes as herein described gives an extra level of specificity to the assay which may be beneficial in certain situations. Furthermore the overall efficiency of light emission for systems employing luminescence energy transfer is believed to be higher than that involving lanthanide emission alone and hence a more sensitive assay will result.

Convenient energy transfer acceptors include certain fluorescent proteins (for example allophycocvanin), certain phthalocyanines, Cy-5 (Biological Detection Systems) and other fluorescent compounds which may be excited by lanthanide emissions. Suitable compounds and means for attaching them to the assay components may be identified using methods and materials outlined above and/or routine experimentation. A convenient appreciation of the issues involved in selection of suitable acceptors, and of the distances between donor and acceptor, is provided by Selvin op cit.

In a further aspect an energy transfer acceptor conjugated to a duplex binder. This novel entity will bind to the duplex DNA in the vicinity of the luminescent lanthanide complex, accept the energy from the lanthanide emission and emit light. The efficiency of light emission for systems employing luminescence energy transfer is believed to be higher than that involving lanthanide emission alone and hence a more sensitive assay will result.

Alternatively multiplex testing is conveniently effected using different emission spectra i.e. using excitation wavelengths and/or different lanthanides to distinguish between the hybridisation products at different target polynucleotides. Examples of suitable systems will be apparent to the scientist of ordinary skill.

Whilst we do not wish to be bound by theoretical considerations the number of target polynucleotides which may be detected simultaneously is limited principally by practical considerations.

8. Further Features

A further feature of the invention is the use of one or more control reactions to ensure the validity of the results obtained. A particular control reaction is provided by the use of a control polynucleotide producing upon hybridisation a different emission spectrum to be detected.

In a still further aspect of the invention measurement of the rate of signal change during hydridisition may be used for diagnostic purposes. By way of non-limiting example the rate of signal change may be indicative of target polynucleotide copy number. This could for example indicate whether an individual is homozygous or heterozygous for a particular allele of a genetic locus. Alternatively it could indicate the presence of a mutant allele against a background of normal alleles. This may be of particular interest in the detection and diagnosis of cancer. The rate of signal change may also reflect the composition of the hybridisation probe and its target polynucleotide and is a useful analytical tool. As previously mentioned the methods of the invention are of particular use in conjunction with the Amplification Refractory Mutation Systems (ARMS). One or more ARMS amplification primers may be provided with signalling components for use in the invention. Alternatively the products of ARMS amplification are used as the target polynucleotide for analysis.

Convenient assay formats include multiplex reactions. If information is required regarding individual mutations then separate sample aliquots are analysed for example on different microtitre plates. Alternatively, in a preferred aspect of the invention, analytes are held and moved within a closed system such as provided by the "pouch" technology developed by Eastman Kodak. This may reduce contamination and aid the interpretation of results.

9. Assay Kits

The invention also relates to assay kits for the detection of analytes such as target polynucleotides. Such kits conveniently comprise more than one of the following features i.e. one or more (i) polynucleotide probe(s), (ii) sensitiser(s), (iii) intercalator(s), (iv) linked intercalator—sensitiser(s), (v) buffers, (vi) PCR amplification primers and (v) instructions for use. Some or all of the assay components may be present at the start of any amplification procedure, for example the primers and/or probe(s) and/or intercalator and/or (linked) sensitiser.

The above kits are conveniently adapted for use in the methods of the invention. By way of non-limiting example the kits may comprise a "pouch" system or single reaction vessel and/or microtitre plates. The above species preferably comprise light transparent vessel(s) to facilitate signal detection.

10. Sequence-dependent intercalation

It is clear from the foregoing that the second component of the energy transfer system is localised, by intercalation, within a specific, proximate distance of the first component. It will be appreciated that the nucleotide sequence of the polynucleotide probe may be adapted so that a signal is only produced when probe binding is correct. That is to say one or more potential regions of non-complementarity may be incorporated into the polynucleotide probe sequence so that when diagnostic mismatches are present upon hybridisation with the target polynucleotide intercalation cannot occur and no signal is produced. If desired additional destabilising mismatches may be employed to increase the sensitivity of this embodiment.

11. Instrumentation

The methods of the invention may employ a variety of instrumentation for measuring fluorescence, depending on the format of the assay. For assays performed in microtitre plates fluorimeters capable of measuring time-resolved fluorescence in plates are preferred, for example the DELFIA fluorimeter (Wallac). Alternatively, suitable fluorimeters for cuvettes and tubes are available. For measuring PCR and ARMS products instrumentation may be devised for measuring the signal in the amplification vessel without having to open the vessel (and optionally during the course of the amplification reaction). This avoids contamination problems.

BRIEF DESCRIPTION OF THE DRAWINGS

The invention will now be illustrated but not limited by reference to the following Figures and Examples wherein:

[In FIGS. 2–6 above intensity is shown on the Y axis and wavelength in nanometres on the X axis.]

METHODS AND MATERIALS

Figure 1:
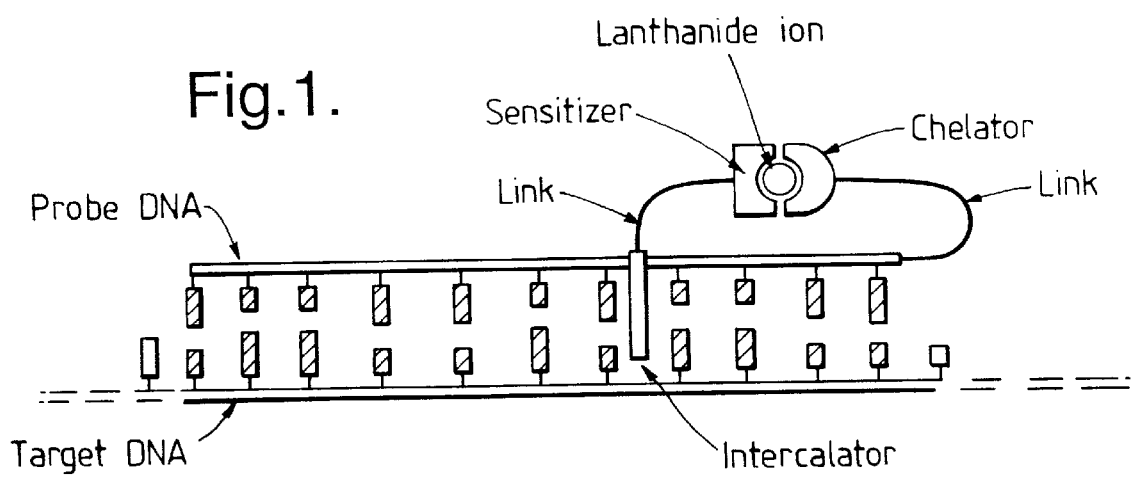
FIG. 1 illustrates binding of probe DNA to target DNA. The intercalator, link, sensitizer, lanthanide ion, chelator and the link between chelator and probe DNA are shown.

Preparation of the Probe nucleotide (1):

This was achieved using an Applied Biosystems polynucleotide synthesiser using the phoshoramidite method. A 6-aminohexyl group was introduced onto the 5'-terminal phosphate group, to give structure (1) by use of an extra cycle of phosphoramidite synthesis with 9-fluorenylmethoxycarbonylaminohexyl beta-cyanoethyl N,N'-diisopropyl-aminophosphite in the coupling reaction.

Preparation of Chelator (2):

The oligonucleotide (1) (250 μl, $10^{-6}$M), was adjusted to pH 7.5 by first adding 100 ul 10 mM $Na_2CO_3$ and then adding dilute HCl (0.1M). The solution was stirred with EDTA bis anhydride (25×) at room temperature for 5 h. To the stirred solution was then added $EuCl_3.6H_2O$ (25×) and stirring continued for another 5 h. The mixture was centrifuged and the supernatant liquid was passed through a Sephadex column (NAP 5 column, Pharmacia), using a 10 mmol Tris buffer, adjusted to pH7.5 with 0.1M HCl, as eluant and collecting 50 μl fractions. Fractions were monitored by absorbance at 260 nm; those fractions showing absorbance were combined and stored at 2° C. until required.

Preparation of the Intercalator (3):

a. 5-Nitro-2,9-dimethylphenanthroline (4) Neocuproine (2,9-dimethylphenanthroline hemihydrate; 10 g) was added to cold fuming sulphuric acid (44 ml) in portions with stirring at room temperature and then fuming nitric acid (50 ml) added before heating the solution at 140° C. under nitrogen for 1 h. After this time the reaction mixture was cooled and poured cautiously onto crushed ice, before neutralising with solid sodium carbonate to pH6. The yellow solid produced was collected and purified by reprecipitation from 3M sulphuric acid solution to give the nitrated product (4) (6.6 g, 50%), m.p. 176°–180° C. (dec.). The material analysed as the hemihydrate; Calcd. for $C_{14}H_{11}N_3O_2.1/2H_2O$: C, 64.12; H, 4.60; N, 16.02. Found: C, 64.52; H, 4.23; N, 15.68%.

b. 5-Nitro-2,9-bis-(trichloromethyl)-1,10-phenanthroline (5) The nitro compound (4) (5.06 g, 20 mmol) in carbon tetrachloride (150 ml) and chloroform (25 ml) was heated at reflux in the presence of N-chlorosuccinimide (18.7 g, 140 mmol) and a catalytic amount of 3-chloroperbenzoic acid. After 24 h the mixture was cooled to room temperature and filtered. The filtrate was washed several times with 10% w/v sodium carbonate solution, dried and the solvent removed to give the crude product; a further crop was obtained from the filtered solids by trituration with chloroform and treating in a similar fashion, to give a total yield of 7.08 g (77%) Material (5) was obtained analytically pure by column chromatography through silica gel using chloroform as eluant. The pure material showed m.p. 228°–231° C. Found: C, 36.16; H, 1.11; N, 8.91. $C14H5N3O2Cl6$ requires C, 36.56; H, 1.10; N, 9.14%.

c. 5-Nitro-1,10-phenanthroline-2,9-dicarboxylic acid (6)
The hexachloride (5) (1.5 g, 3.3 mmol) was mixed with 98% sulphuric acid (8 ml) and heated to between 80°–90° C. under nitrogen. After 6 h the viscous solution was poured over crushed ice, precipitating the diacid as a pale yellow solid. The solid was collected and recrystallised from hot aqueous tetrahydrofuran to give the pure diacid (0.9 g, 89%); m.p. 218°–220° C., Found: C, 52.46; H, 2.77; N, 12.95. $C_{14}H_7N_3O_6.1/2H_2O$ requires C, 52.18; H, 2.50; N, 13.04%.

d. 5-Nitro-2,9-bis(methoxycarbonyl)-1,10-phenanthroline (7)
The hexachloride (5) (2.0 g, 4.35 mmol) was mixed with 98% sulphuric acid (5 ml) and heated to 90° C. under nitrogen for 2 h. The mixture was cooled in ice and then added slowly to methanol (10 ml) After heating at reflux for a further 45 min, the excess of methanol was removed in vacuo and the residue neutralised to pH 6–7 with saturated aqueous sodium carbonate solution. The crude product was collected by vacuum filtration and dried to give the pure diester (1.27 g, 86%); m.p. ca. 260° C. (dec.). Found: C, 56.42; H, 3.24; N, 12.05; $C_{16}H_{11}N_3O_6$ requires C, 56.31; H, 3.24; N, 12.31%.

e. 5-Amino-2,9-bis(methoxycarbonyl)-1,10-phenanthroline (8) The nitro compound (7) (1.0 g, 3 mmol) in methanol (100 ml) was heated with cyclohexene (1.4 g, 17 mmol) and Pd/C10%, 0.2 g) and reflux continued for 3 h. The mixture was cooled and filtered through Celite, washing the residues with more methanol (50 ml) until no more colour exuded. The combined filtrates were evaporated to afford the product amine as a bright yellow solid (0.73 g, 77%); m.p. ca. 240° C. (dec.) M/e 311 (M+; 57%), 253 (86), 195(56).

f. 5-Amino-1,10-phenanthroline-2,9-dicarboxylic Acid (9) The nitro-diacid (6) (0.3 g, 0.93 mmol) in formic acid (15 ml) was treated with Pd/C (10%, 0.3 g) and the mixture heated to reflux for 2 days under nitrogen. The mixture was cooled, filtered and the solids washed with more formic acid (10 ml) before collecting the filtrate and evaporating off the solvent formic acid to yield the product amine as an orange solid (0.26 g, 96%). This material was extremely insoluble in most organic solvents. It was characterised by conversion to the corresponding dimethyl ester (8). Thus a small sample (30 mg) of the acid (9) was stirred in methanol (3 ml) containing one drop of 98% sulphuric acid at room temperature for 16 h. The solution was neutralised with solid sodium hydrogen carbonate, filtered and the solvent removed to yield the diester (8), identical in its physical and chromatographic behaviour to the material described above.

g. 5-(6-Bromohexanoyl)amino-2,9-bis(methoxycarbonyl) -1,10-phenanthroline (10) The amine (8) (0.5 g, 1.6 mmol) was reacted with 6-bromohexanoyl chloride (0.425 g, 2 mmol) in dry chloroform (5 ml) containing an excess of Hunig's base. After stirring at room temperature for 2 h the solution was washed with water and dilute HCl and, finally, water before drying, filtering and evaporation of the solvent to afford the amide, (0.65 g, 85%), m.p. 129°–132° C. dec.); Found: C, 52.18; H, 4.66; N, 8.24; Br, 15.91. $C_{22}H_{22}N_3O_5Br.H_2O$ requires C, 52.18; H, 4.77; N, 8.30; Br, 15.78%.

h. 5-[6-(N-Phenanthridinium)hexanoyl]amino-2,9-bis (methoxycarbonyl)-1,10-phenanthroline Bromide (11) Phenanthridine (0.52 g, 2.9 mmol) was heated to 120° C. under nitrogen to its melting point and then, to the melt was added, portionwise over 10 minutes, the bromide (10) (0.525 g, 1.04 mmol). The mixture was heated at 120° C. for 90 min before cooling and dissolving the solid product in chloroform (8ml). To the solution was added ether (15 ml) to form a yellow precipitate, which was collected by filtration to give the salt (11) (0.677 g, 95%). The product was recrystallised from water to give pale yellow needles of the monohydrate, m.p. 160° C. (dec.). Found: C, 61.45; H, 4.66; N, 8.23. $C_{35}H_{31}N_4O_5Br.H_2O$ requires C, 61.32; H, 4.85; N, 8.17%.

i. 5-[6-(N-phenanthridinium)hexanoyl]amino-1,10-phenanthroline-2,9-dicarboxylic Acid Bromide (3) The dimethyl ester (11) (0.10 g, 0.15 mmol) was added to distilled water (7 ml), the pH adjusted to 4 with dilute HBr and the mixture heated to reflux, whereupon the solid slowly dissolved to produce a yellow solution. After 20 h the solution was filtered to remove traces of solid, and then freeze dried to give the required acid (50 mg, 52%), m.p. >180° C. (dec.). The material was characterised by re-esterification with methanol under HBr acid catalysed conditions to reform the ester (11).

Preparation of the intercalator (12)

j. 4-(Nitrophenyl)-2,9-dimethyl-1,10-phenanthroline (13) 4-Phenyl-2,9-dimethyl-1,10-phenanthroline (0.5 g, 1.75 mmol) in 98% sulphuric acid (4 ml) was cooled to <10° C. in an ice-salt bath before adding, dropwise, a mixture of 98% sulphuric acid (1 ml) and 65% nitric acid (1 ml) keeping the temperature below 15° C. After addition the mixture was allowed to warm to ambient over 20 min before pouring onto crushed ice and then neutralising with 7N sodium hydroxide to pH 7, to produce a beige precipitate. The precipitate was extracted into chloroform (3×25 ml) washed with brine (25 ml), dried, filtered and evaporated to give the product as a mixture of ortho-, meta- and para-nitrophenyl isomers (0.58 g, 100%).

k. 4-(Nitrophenyl)-2,9-bis(trichloromethyl)-1,10-phenanthroline (14) The nitro-compound (13) (0.5 g, 1.6 mmol) was dissolved in chloroform (5 ml) and then diluted with carbon tetrachloride (30 ml). To the solution was added N-chlorosuccinimide (1.54 g, 11.5 mmol) and a catalytic amount of 3-chloroperoxybenzoic acid. This mixture was heated overnight at reflux, cooled and filtered, washing the solids with chloroform. The filtrate was washed with 5% w/v sodium carbonate solution (3×30 ml), 0.1M sodium thiosulphate solution (50 ml), brine (50 ml) and then dried and filtered. The solvent was removed to leave a yellow solid which was chromatographed through silica gel, using 4:6 dichloromethane-light petroleum ether as eluant. The main fraction yielded the bis(trichloromethyl) derivative (14) (0.81 g, 91%), m.p. >180° C. (dec.).

l. 4-(Nitrophenyl)-2,9-bis(methoxycarbonyl)-1,10-phenanthroline (15) The hexachloride (14) (1.00 g, 1.86 mmol) was dissolved in 98% sulphuric acid (2.5 ml) and heated to 90° C. under nitrogen for 2 h. The mixture was then cooled in an ice-salt bath before carefully quenching into methanol (6 ml). The solution was heated to reflux for 45 min before cooling and quenching with crushed ice. The mixture was neutralised with 7N sodium hydroxide solution and the off-white precipitate was collected and dried before recrystallisation from methanol/chloroform to give the nitrodimethyl ester as a monohydrate (0.60 g, 77%).

m. 4-(Aminophenyl)2,9-bis(methoxycarbonyl)-1,10-phenanthroline (16) The nitrodiester (15) (0.25 g, 0.6 mmol) was slurried in methanol (50 ml) and cyclohexene (5 ml) and 10% Pd/C (50 mg) added. The mixture was heated under reflux under nitrogen for 16 h before cooling and filtering through Celite. The solids were washed with hot chloroform (30 ml) and the combined filtrate reduced to small bulk to yield a red solid. The product was purified by chromatography through silica gel, using 2% v/v methanol in chloroform as eluant. The product was obtained as the monohydrate (90 mg, 35%).

n. Conjugation of Acridine with the amine (16) The amine (16) (39 mg, 0.1 mmol) in dry chloroform (2 ml) was heated with 9-chloroacridine (50 mg, 2.35 mmol) at reflux for 5 h. Diethyl ether (25 ml) was added to precipitate, as an orange crystalline solid, the target ester (17) (40 mg, 65%).

o. Hydrolysis of the Ester (17) The ester (17) (25 mg) was heated in distilled water at reflux for 5 h. The solution was cooled to afford a crystalline solid which was collected and dried to afford the target intercalating acid (12) (20 mg).

Preparation of the Intercalator (18)

p. 4-(4-Bromobutoxy)-2,9-dimethyl-1,10-phenanthroline (20) 4-Hydroxy-2,9-dimethyl-1,10-phenanthroline (19) (2.0 g, 5.9 mmol) was heated in refluxing acetonitrile (50 ml) in the presence of 1,4-dibromobutane (10 g) and potassium carbonate (2.0 g). After 10 h the solution was filtered, the solvent removed and the residue triturated with chloroform-diethyl ether to afford the title compound (20) as a solid (2.5 g). This was used without further purification.

q. 4-(4-Bromobutoxy)-2,9-bis(trichloromethyl)-1,10-phenanthroline (21) To the ether (20) (0.4 g, 1.11 mmol)) in refluxing carbon tetrachloride (30 ml) was added N-chlorosuccinimide (98 mg, 7.33 mmol) and a catalytic amount of 3-chloroperoxybenzoic acid. After 12 h at reflux the solution was cooled, filtered and the solvent evaporated from the filtrate to leave a pale yellow residue which was chromatographed through silica gel, using 1:1 benzene:acetone as eluant, to give the title compound (0.50 g, 70%), m.p >150° C. (dec.). Found: C, 37.74; H, 2.32; N, 4.95; $C_{18}H_{13}N_2Cl_6BrO$ requires C,38.20; H, 2.32; N, 4.95%.

r. 4-(4-Bromobutoxy)-1,10-phenanthroline-2,9-dicarboxylic Acid (22) The hexachloride (21) (0.4 g, 0.7 mmol) was heated in aqueous acetic acid (1:4) (50 ml) at reflux. Portions of sodium acetate (3×350 mg, anhydrous) were added at 30 min intervals and heating continued for a total of 12 h. The solution was filtered and the bulk of the solvent removed by evaporation under reduced pressure to leave a fine powder which was recystallised from aqueous tetrahydrofuran to give the acid (80 mg, 27%). M.p >180° C. (dec.). Found: C, 49.31; H, 3.68, N, 6.93. $C_{18}H_{17}N_2O_5Br.H_2O$ requires C, 49.45; H, 3.92; N, 6.91%.

s. 4-[4-(N-Phenanthridinium)butyloxy)-1,10-phenanthroline-2,9-dicarboxylic Acid Bromide (18). The acid (22) (50 mg, 0.11 mmol) was heated under nitrogen in phenanthridine (150 mg) at its melting point whilst stirring with a small spatula. After 20 minutes the mixture was cooled to room temperature and triturated with diethyl ether to afford a light brown solid (40 mg). The solid was sparingly soluble in water. No molecular ion could be observed in its mass spectrum.

EXAMPLE 1

Figure 2:
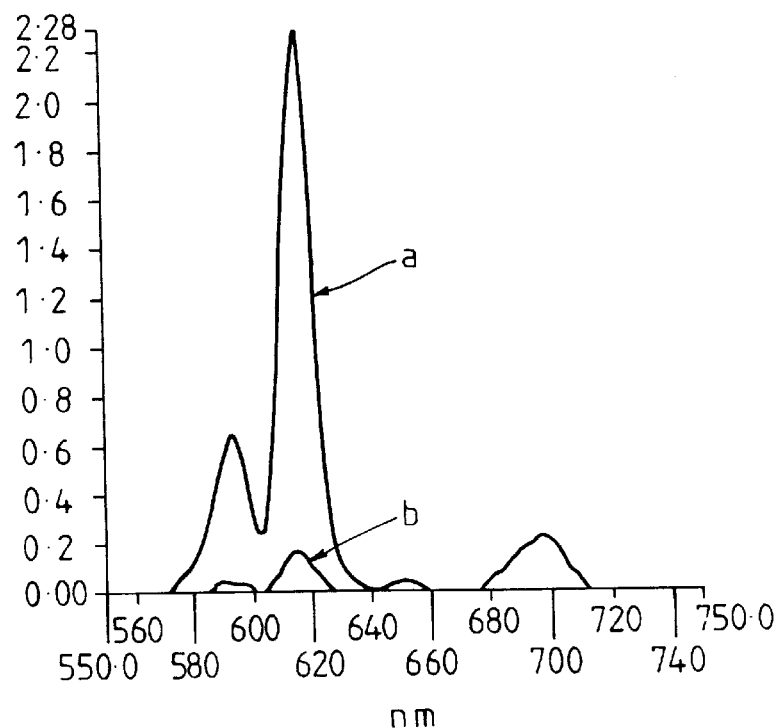
FIG. 2 shows the output of the assayed solution described in Example 1 at 112× dilution and with a concentration of probe and targets at approximately $1.7 \times 10^{-8}$M. Curve a is with matching target A and curve b is with non-matching target B.

Assay Procedure:

A sample of the europium (III) complex of the probe (2) (100 μl, $1.75\times10^{-5}$M) was added to a solution of the target material (A) (200 μl, $2.6\times10^{-5}$M) and Denhardt's solution (100 μl) and the volume made up to a total of 1 ml with buffer solution (0.01 MM Tween 20, 1M NaCl, 0.1M HEPES). The solution was hybridised by heating to 42° C. for 3 h before cooling to room temperature. To the solution was added the sensitiser (1 ml, $1\times10^{-5}$M in buffer) and the solution kept at room temperature for 1 hour before being serially diluted (up to ×448), with the buffer and measurements of luminescence made by irradiating at 290 nm and measuring the delayed emission in the region around 615 nm. FIG. 2 shows the output of the assayed solution at ×56 dilution [concentrations: Target, $4.46 \times 10^{-8}$M, Probe: $1.56 \times 10^{31}\ ^8$M; Sensitiser: $8.9 \times 10^{-8}$M]. The reference solution consisted of the probe polynucleotide and intercalator at the same concentration but in the presence of the unrelated target (B)

EXAMPLE 2

As a further test of the above assay procedure we used probe 3284 (SEQ ID No:1) (GAGATCAACGAGCAAGAATTTCTT) and 3 different targets ie. matched 3288 (SEQ ID No:2) (GCTAAAGAAATTCTTGCTCGTTGATCTCCACT), mismatched 2638 (SEQ ID No:3) (GATCATTCATGACATTTTAAAAATTACAGG) and one base pair different 3287 (SEQ ID No:4) (GCTAAAGAAATTCTTGCTCGTTGACCTCCACT).

The same procedures for labelling, purifying and hybridisation was followed as before. The results are shown below.

| CONC. | 3288 | 3287 | 2638 |
|---|---|---|---|
| $4.1 \times 10^{-6}$M | 28 | 15 | 0.8 |
| $8.2 \times 10^{-7}$M | 9 | 1.52 | 0.27 |
| $8.2 \times 10^{-8}$M | 1.12 | 0.05 | <0.04 |
| $8.2 \times 10^{-9}$M | 0.2 | <0.02 | <0.01 |

It can be seen that there is a clear distinction between the three oligonucleotides ie. 3288 (matched), 3287 (one base pair mismatched) and 2638 (mismatched). Not only is there discrimination between matched and mismatched oligonucleotides but also the one base pair different oligonucleotide produced less counts than the matched oligonucleotide. This also occurred at varying dilutions. It can be seen that, at concentrations approaching $4 \times 10^{-9}$M there is a significant difference between the three targets. The distinction improves with dilution.

EXAMPLE 3

Assay procedure using PCR products:

The synthesis of the europium labelled probe 3284 (SEQ ID No:1) (GAGATCAACGAGCAAGAATTTCTT) is as previously outlined. To test the G551D-europium (mutant specific) oligonucleotide probe, polymerase chain reaction (PCR) products were required.

1) Mutant sequence only, Exon 11 homozygote
2) Mutant and normal sequence, Exon 11 heterozygote
3) Normal sequence, Exon 11 wild type
4) Unrelated normal sequence, Exon 10 wild type PCR primers that would amplify the exon 11 and the exon 10 regions of genomic DNA were synthesized:

Exon 11: 152 bp product spanning the G551D mutation site

Exon 10: 216 bp product spanning the DF508 mutation site

Exon 11 primers vs. G551D/G551D homozygote genomic DNA

_____×_____G551D mutant template (152 bp)

_____×_____G551D mutant template (152 bp)

Exon 11 primers vs. G551D/normal heterozygote DNA

_____×_____G551D mutant template (152 bp)

_____Normal template (152 bp)

Exon 11 primers vs. normal/normal DNA

_____Normal template (152 bp)

_____Normal template (152 bp)

Exon 10 primers vs. normal/normal DNA

_____Normal template (216 bp)

_____Normal template (216 bp)

Reaction of PCR products

| Reaction Mix | | |
|---|---|---|
| Exon 11 | H$_2$O | 2240 μl |
| | 10X ARMS Buffer | 400 μl |
| | 1 mM dNTP's | 400 μl |
| | 50 μM 3108 primer | 80 μl |
| | 50 μM 3109 primer | 80 μl |
| | Aliquot: | 60 × 40 μl |
| | Tube numbers: | 1, 2, 3 (×20 each) |
| Exon 10 | H$_2$O | 700 μl |
| | 10X ARMS Buffer | 125 μl |
| | 1 mM dNTP's | 125 μl |
| | 50 μM 2090 primer | 25 μl |
| | 50 μM 2091 primer | 25 μl |
| | Aliquot: | 20 × 40 μl |
| | Tube Number: | 4 (×20) |

DNA Dilutions

The template for the reaction will be product amplified previously. The PCR product will be diluted so that approximately 10,000 copies are added to each new reaction.

Exon 11 product:

$1.0032 \times 10^{-5}$ (molecular weight) = $1.66561 \times 10^{-19}$ g = 1 molecule
$6.023 \times 10^{23}$ (Avogadro's number)

Exon 10 product:

$1.4356 \times 10^5$ (molecular weight) = $2.36692 \times 10^{-19}$ g = 1 molecule
$6.023 \times 10^{23}$ (Avogadro's number)

| | | |
|---|---|---|
| GD/GD product: 8 ng · μl$^{-1}$ | $8 \times 10^{-9}$ g | = $4.8 \times 10^{10}$ molecules/μl |
| | $1.665161 \times 10^{-19}$ g | |
| GD/+ product: 7 ng/μl$^{-1}$ | $7 \times 10^{-9}$ g | = $4.2 \times 10^{10}$ molecules/μl |
| | $1.665161 \times 10^{-19}$ g | |
| +/+ (Ex11) product: 6 ng · μl$^{-1}$ | $6 \times 10^{-9}$ g | = $3.6 \times 10^{10}$ molecules/μl |
| | $1.66561 \times 10^{-19}$ g | |
| +/+ (Ex10 product: 6 ng · μ$^{-1}$ | $6 \times 10^{-9}$ g | = $2.53 \times 10^{10}$ molecules/μl |
| | $2.36692 \times 10^{-19}$ g | |

Electrophoresis of PCR products

Following aliquots for each DNA sample were electrophoresed:

| | |
|---|---|
| 1. 10 μl pooled product | 2. 5 μl pooled product |
| 3. 2 μl pooled product | 4. 19 μl 1:10 pooled product |
| 5. 5 μl 1:10 pooled product | 6. 2 μl 1:10 pooled product |
| 7. 10 μl concentrated product | 8. 5 μl concentrated product |
| 9. 2 μl concentrated product | 10. 10 μl 1:10 concentrated product |
| 11. 5 μl 1:10 concentrated product | 12. 2 μl 1:10 concentrated product |

By comparison of PCR product band intensity with band intensity of the ox174/HaeIII molecular weight standards, the following estimates of the DNA concentration of the concentration products were made:

| | | | |
|---|---|---|---|
| GD/GD | 15 ng-μl$^{-1}$ | 150 nM solution | 0.66 μl in 100 μl = 1 × 10$^{-9}$M |
| GD/+ | 10 ng-μl$^{-1}$ | 100 nM solution | 1.00 μl in 100 μl = 1 × 10$^{-9}$M |
| +/+ (Ex11) | 8 ng-μl$^{-1}$ | 80 nM solution | 1.25 μl in 100 μl = 1 × 10$^{-9}$M |
| +/+ (Ex10) | 5 ng-μl$^{-1}$ | 35 nM solution | 2.66 μl in 100 μl = 1 × 10$^{-9}$M |

The products were diluted as follows:

| | | | | |
|---|---|---|---|---|
| Stock | | | | 10$^{10}$ molecular/μl |
| 1. 10 μl product | + | 990 μl H$_2$O | = | 10$^8$ molecular/μl |
| 2. 10 μl (1.) | + | 990 μl H$_2$O | = | 10$^6$ molecules/μl |
| 3. 10 μl (2.) | + | 990 μl H$_2$O | = | 10$^4$ molecules/μl |
| 4. 100 μl (3.) | + | 990 μl H$_2$O | = | 10$^3$ molecules/μl |
| 5 μl of corresponding DNA was added to each reaction mix | | | | |
| GD/GD | | 2.4 × 10$^4$ molecules | | |
| GD/+ | | 2.1 × 10$^4$ molecules | | |
| +/+ (Ex11) | | 1.8 × 10$^4$ molecules | | |
| +/+ (Ex10) | | 1.3 × 10$^4$ molecules | | |

PCR Product Concentration, Purification and Washing

After amplification, PCR products were accordingly pooled, 20 μl of pooled product was set aside for gel analysis. The remaining product was applied to microcon filtration membranes.

400 μl pooled product added to microcon—5000 rpm for 10 minutes

400 μl pooled product added to microcon—5000 rpm for 10 minutes

500 μl H$_2$O added to microcon—5000 rpm for 5 minutes

500 μl H$_2$O added to microcon—5000 rpm for 5 minutes

The DNA was eluted from the membrane by the addition of 180 μl H$_2$O and centrifugation at 3500 rpm for 3 minutes. 20 μl of the concentration product was retained for gel analysis.

| | Results | | | | |
|---|---|---|---|---|---|
| | -VE | GD/GD | EX10++ | GC/+ | EX11++ |
| INt | 7.1 | 38.5 | 21.1 | 35 | 18.5 |

(using the same probe 3284)

EXAMPLE 4

A further example of the use of the lanthanide enhanced signalling system of the invention was obtained by hybridisation of the oligonucleotide probe 3922 (SEQ ID No:5) (GAGGTCAACGAGCAAGAATTTCTTGC) to the oligonucleotide targets 3860 (SEQ ID No:6) (GCTAAAGAAATTCTTGCTCGTTGACCTCCACT) and 3288 (SEQ ID No:2) (GCTAAAGAAATTCTTGCTCGTTGATCTCCACT). Target 3860 comprises normal DNA sequence obtained from exon 11 of the CFTR gene which is unaffected by the G551D mutation. Target 3288 is comprises CFTR exton 11 sequence containing the G551D mutation. The 5' 24 bases of probe 3922 are complementary to a sequence contained within target 3860. 23 of the 24 bases at the 5' terminus of probe 3922 are complementary to target 3288 but the guanosine residue at position 5'-4 is mis-matched to a thymidine residue in that target.

Figure 3:
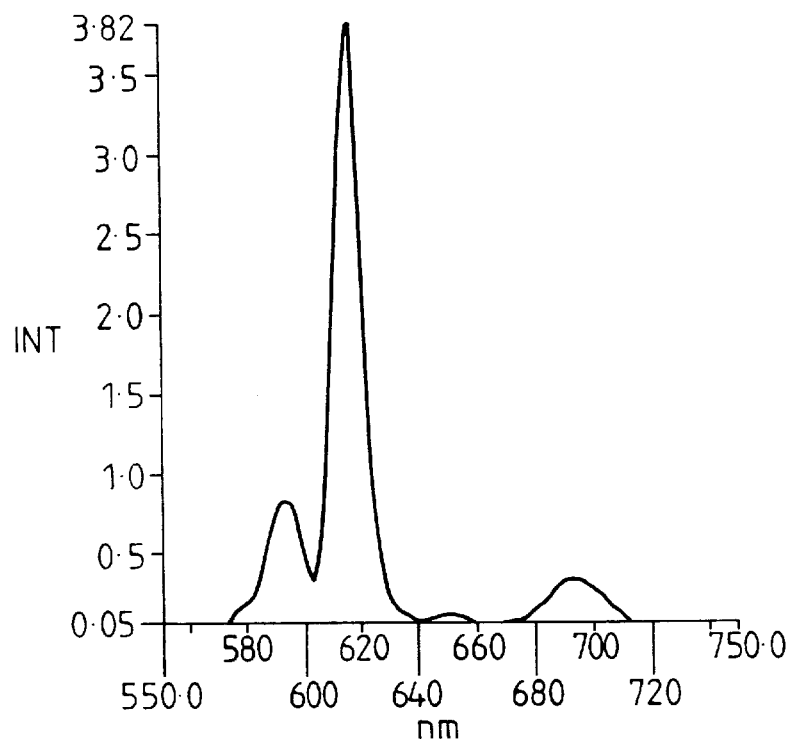
FIG. 3 shows the output of the assayed solution described in Example 4 with normal Target 3860 and normal Probe 3922, both at $2 \times 10^{-7}$M concentration.
Figure 4:
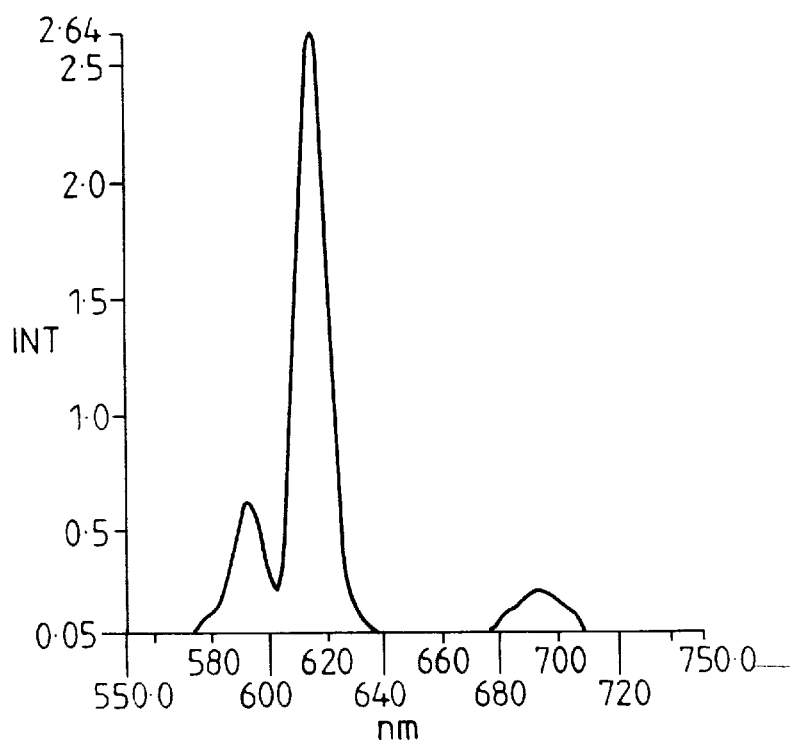
FIG. 4 shows the output of the assayed solution described in Example 4 with mutant Target 3288 and normal Probe 3922, both at $2 \times 10^{-7}$M concentration.
Figure 5:
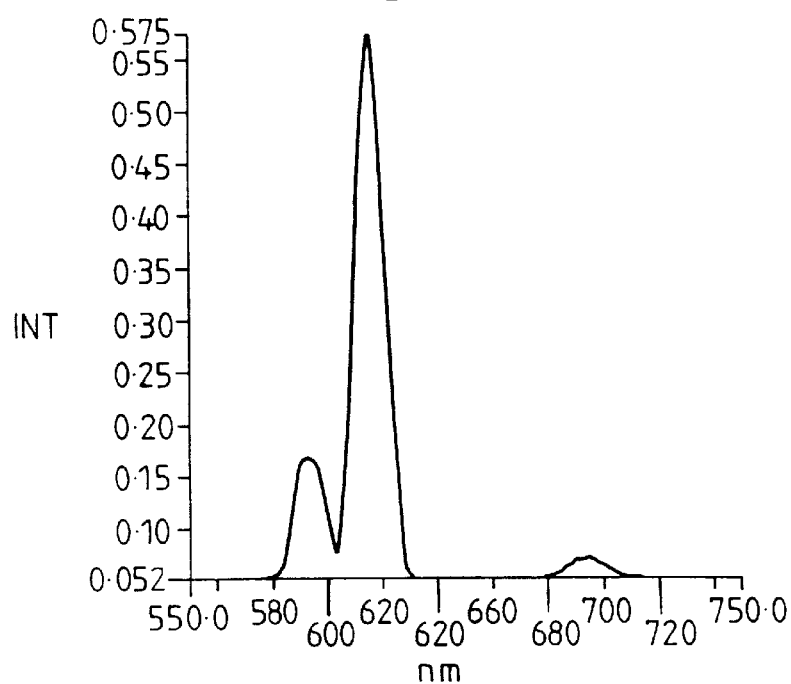
FIG. 5 shows the output of the assayed solution described in Example 4 with normal Probe 3922 at $2 \times 10^{-7}$M concentration. No target was present.
Figure 6:
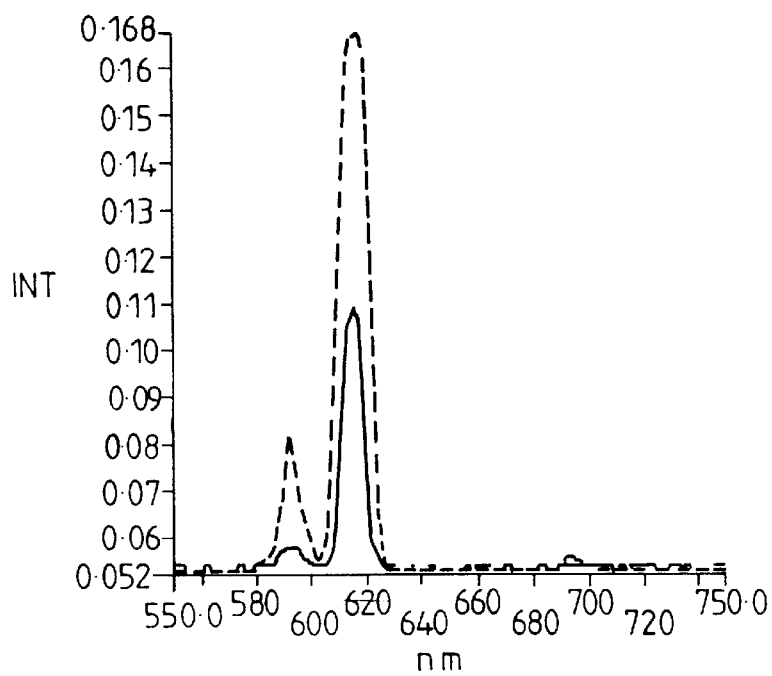
FIG. 6 shows the output of the assayed solution described in Example 4 at 64× dilution (i) with normal Probe 3922 and mutant Target 3288, both at $3.1 \times 10^{-9}$M concentration [solid line] and (ii) with normal Probe 3922 and normal Target 3860, both at $3.1 \times 10^{-9}$M concentration [dotted line].

The procedures for labelling, purification and hybridisation are as described above. Hybridisation reactions were effected with equimolecular ratios of probe, target and intercalator and concentrations of 2×10$^{-7}$M. A negative control hybridisation contained no target oligonucleotide. The results obtained are shown in FIGS. 3–5. The solutions were diluted to 3.1×10$^{-9}$M (i.e. ×64) and new readings were obtained as shown in FIG. 6.

The data shows a clear discrimination between targets 3860 and 3288 by probe 3922. A greater hybridisation signal is generated by probe 3922 when it is perfectly matched to its target at its 5' terminus (3860) than when it is mis-matched (3288). Discrimination between targets 3860 and 3288 improves in the 64× dilutions and background signal from the no target control was undetectable at this dilution.

It should be noted that a further design feature of probe 3922 is that its 3' terminus and penultimate bases are mis-matched to both targets 3860 and 3286. These mis-matches have been introduced into probe 3922 to destabilise the 3' terminus of that probe causing it to be refractory to amplification in the PCR or other gene amplification systems. Probe 3922 may therefore be included in PCR reactions which have been designed to amplify exon 11 of the CFTR gene without the probe serving as a PCR primer itself. Alternatively, blocking groups or dideoxynucleotides may be included at the 3' terminus of such probes to prevent their extension by Taq polymerase during the PCR.

The chemical formulae referred to in the application text above are as follows:

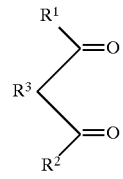

I

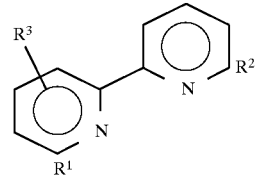

II

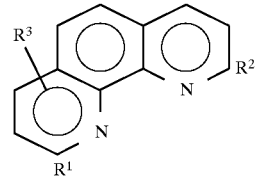

III

INTERCALATOR-LINK-SENSITISER    IV

SEQ ID no:7 GTGGTAATTTCTTTTATAGTAGAA—O(CH$_2$)$_6$NH$_2$

Probe-NH₂     1
$$\text{Probe-NHCCH}_2\text{NCH}_2\text{CH}_2\text{NCH}_2\text{CO}_2\text{H}$$
with CH₂CO₂H branches     2
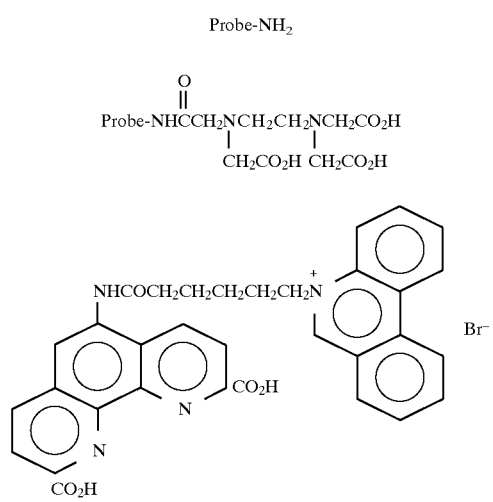
3
Target A (SEQ ID no:8): 5' CAC.CAT.TAA.AGA.AAA.TAT.CAT.CTT 3'
Target B: (SEQ ID no:9): 5' GGG.GAA.TCA.CCT.TCT.GTC.TAC.AAT 3'
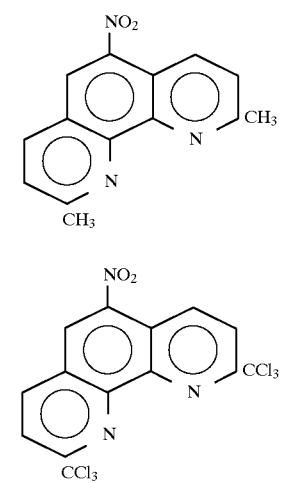
4, 5
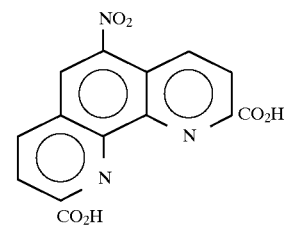
6
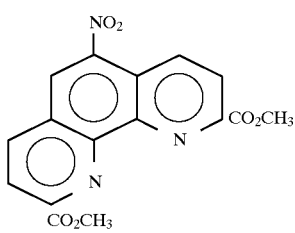
7
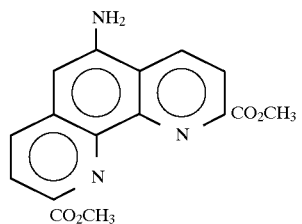
8, 9, 10, 11, 12

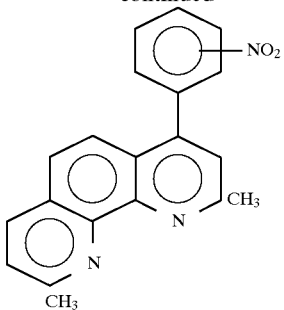
13
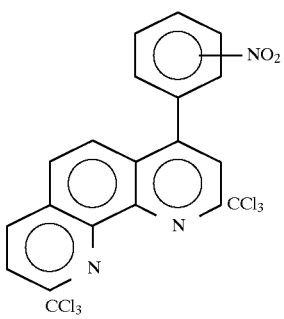
14
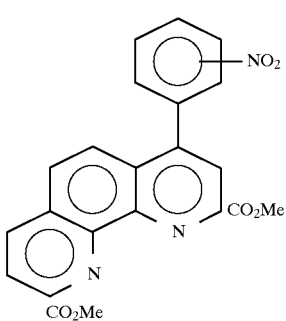
15
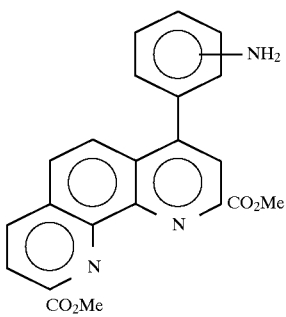
16
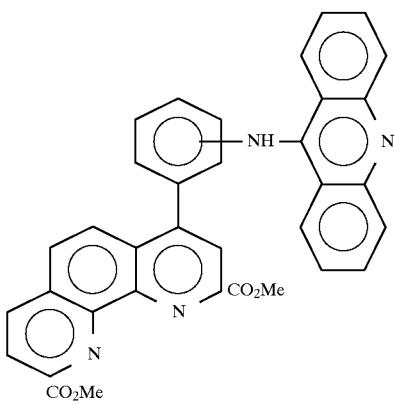
17
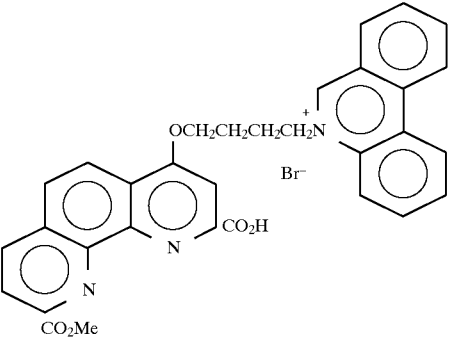
18
---

We claim:

1. A method for detecting a nucleic acid analyte in a sample, which method comprises contacting the sample with (i) a binding entity complementary to the analyte and to which is attached a first partner of a ligand to metal energy transfer system, (ii) a lanthanide ion, and (iii) a second partner of the system to which is attached a duplex binder; wherein the first partner of the ligand to metal energy transfer system is a complexing sensitiser and the second partner is a chelating agent, or vice versa; such that upon complementary binding of the analyte and the binding entity to form a nucleic acid duplex, interaction of the duplex binder with the duplex occurs and allows the first and the second partners of the system to form a closed chelated system around the lanthanide ion and, upon irradiation, emission of light from the lanthanide ion indicates the presence of the analyte in the sample.

2. A method as claimed in claim 1 wherein the duplex binder is selected from the group consisting of an intercalator and a groove binder.

3. A method as claimed in claim 1 wherein the binding entity is a polynucleotide to which the first or the second partner is attached.

4. A method as claimed in claim 3 wherein the binding entity comprises a blocked terminal nucleotide.

5. A method as claimed in any one of the previous claims wherein the binding entity comprises one or more mismatched bases opposite a complementary analyte nucleic acid sequence.

6. A method as claimed in claim 5 wherein a position of the one or more mismatched bases is selected such that duplex binding and hence formation of the closed chelated system around the lanthanide ion are modulated.

7. A method as claimed in claim 1 wherein the lanthanide ion is an europium ion.

8. A method as claimed in claim 1 wherein the complexing sensitiser comprises an aromatic group.

9. A method as claimed in claim 1 wherein the complexing sensitiser comprises a heterocyclic aromatic group.

10. A method as claimed in claim 1 wherein the complexing sensitiser comprises an optionally substituted dipyridyl or phenanthroline group.

11. A method as claimed in claim 1 wherein the complexing sensitiser comprises an optionally substituted phenanthroline-2,6-dicarboxylic acid group.

12. A method as claimed in claim 1 wherein the chelating agent is chelated with the lanthanide ion before addition to the assay medium.

13. A method as claimed in claim 1 wherein the binding entity is a polynucleotide to which a chelated lanthanide ion is attached.

14. A method as claimed in claim 1 wherein one partner of the ligand to metal energy transfer system is a complexing sensitiser linked to a duplex binder.

15. A method as claimed in claim 1 wherein the binding entity is an allele-specific polynucleotide.

16. A method as claimed in claim 1 which comprises amplification of a target sequence to provide the nucleic acid analyte.

17. A method as claimed in claim 16 wherein one or more components of the method are present during amplification of the target sequence.

18. A method as claimed in claim 1 wherein the binding entity is comprised of two or more polynucleotide sequences.

19. A method as claimed in claim 18 wherein the first and the second partners of the ligand to metal energy transfer system are attached to different polynucleotide sequences.

20. A method as claimed in claim 1 wherein the chelating agent is a polyfunctional compound comprising carboxylic acid, amide and/or ether moieties.

21. A method as claimed in claim 20 wherein the chelating agent is a derivative of a compound selected from the group consisting of ethylenediaminetetraacetic acid (EDTA), diethylenetriaminepentaacetic acid (DTPA) and trans-1,2-diaminocyclohexanetetraacetic acid (DCTA).

22. A method as claimed in claim 1 wherein a Förster energy transfer acceptor is used to receive energy from the closed chelated system around the lanthanide ion and to emit light.

23. A method as claimed in claim 22 wherein the Förster energy transfer acceptor is bound to a polynucleotide.

24. A method as claimed in claim 1 for detection of more than one nucleic acid analyte in a sample.

25. A method as claimed in claim 1 wherein the characteristics of light emission are measured to indicate the nature and/or quantity of the nucleic acid analyte.

26. A method as claimed in claim 1 which is a homogeneous assay.

27. An assay kit which comprises (i) a binding entity complementary to the analyte and to which is attached a first partner of a ligand to metal energy transfer system, (ii) a lanthanide ion, (iii) a second partner of the system to which is attached a duplex binder; wherein the first partner of the ligand to metal energy transfer system is a complexing sensitiser and the second partner is a chelating agent, or vice versa; and further comprising one or more of the following: buffer(s), amplification primers and instructions for use of the kit.

28. An assay kit as claimed in claim 27 wherein the amplification primers are for allele specific amplification.

29. A compound which comprises a duplex binder covalently linked to a lanthanide ion sensitiser.

30. A compound as claimed in claim 29 which comprises a phenanthroline-2,6-dicarboxylic acid group linked to a phenanthridine group.

31. A compound as claimed in claim 30 of the formula

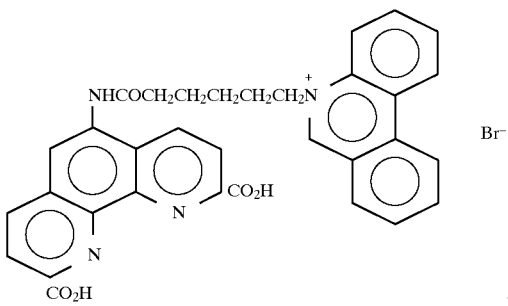

32. A composition which comprises a duplex binder covalently linked to a lanthanide ion chelating agent and a lanthanide ion.

33. A compound as claimed in any one of claims 27 and 29–31 wherein the duplex binder is selected from the group consisting of an intercalator and a groove binder.

* * * * *